(12) United States Patent
Shirotori et al.

(10) Patent No.: US 11,432,751 B2
(45) Date of Patent: Sep. 6, 2022

(54) MAGNETIC SENSOR AND INSPECTION DEVICE

(71) Applicant: KABUSHIKI KAISHA TOSHIBA, Tokyo (JP)

(72) Inventors: Satoshi Shirotori, Kanagawa (JP); Hitoshi Iwasaki, Tokyo (JP); Akira Kikitsu, Kanagawa (JP); Yoshihiro Higashi, Ishikawa (JP); Yoshinari Kurosaki, Kanagawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 0 days.

(21) Appl. No.: 17/399,345

(22) Filed: Aug. 11, 2021

(65) Prior Publication Data

US 2022/0175289 A1 Jun. 9, 2022

(30) Foreign Application Priority Data

Dec. 3, 2020 (JP) .............................. JP2020-201001

(51) Int. Cl.
*G01R 5/00* (2006.01)
*A61B 5/245* (2021.01)
*G01R 33/00* (2006.01)

(52) U.S. Cl.
CPC .......... *A61B 5/245* (2021.01); *G01R 33/0094* (2013.01)

(58) Field of Classification Search
CPC ... A61B 5/245; G01R 33/0094; G01R 33/093
See application file for complete search history.

(56) References Cited

U.S. PATENT DOCUMENTS

| | | | |
|---|---|---|---|
| 11,237,230 B1* | 2/2022 | Iwasaki | G01R 31/382 |
| 2015/0204919 A1* | 7/2015 | Akimoto | G01R 33/0094 324/244 |
| 2015/0316394 A1* | 11/2015 | Kim | G01R 33/0094 324/207.2 |
| 2018/0100902 A1* | 4/2018 | Schott | G01R 33/098 |
| 2018/0271395 A1* | 9/2018 | Iwasaki | A61B 5/245 |
| 2019/0369172 A1 | 12/2019 | Kikitsu et al. | |

FOREIGN PATENT DOCUMENTS

| | | |
|---|---|---|
| JP | 2019-207167 A | 12/2019 |
| WO | WO 2019/239933 A1 | 12/2019 |
| WO | WO 2020/138170 A1 | 7/2020 |

* cited by examiner

*Primary Examiner* — Alvaro E Fortich
(74) *Attorney, Agent, or Firm* — Finnegan, Henderson, Farabow, Garrett & Dunner L.L.P.

(57) ABSTRACT

According to one embodiment, a magnetic sensor includes a first magnetic element, a second magnetic element, a third magnetic element located between the first and second magnetic elements in a first direction, a fourth magnetic element located between the third and second magnetic elements in the first direction, a first conductive member, a second conductive member, a third conductive member located between the first and second conductive members in the first direction, a fourth conductive member located between the third and second conductive members in the first direction, a first magnetic member, a second magnetic member, a third magnetic member located between the first and second magnetic members in the first direction, a fourth magnetic member located between the third and second magnetic members in the first direction, and a fifth magnetic member located between the third and fourth magnetic members in the first direction.

20 Claims, 15 Drawing Sheets

MAGNETIC SENSOR AND INSPECTION DEVICE

CROSS-REFERENCE TO RELATED APPLICATIONS

This application is based upon and claims the benefit of priority from Japanese Patent Application No. 2020-201001, filed on Dec. 3, 2020; the entire contents of which are incorporated herein by reference.

FIELD

Embodiments described herein relate generally to a magnetic sensor and an inspection device.

BACKGROUND

There is a magnetic sensor that uses a magnetic layer. There is an inspection device that uses the magnetic sensor. It is desirable to increase the sensitivity of the magnetic sensor.

DETAILED DESCRIPTION

Figure 1A:
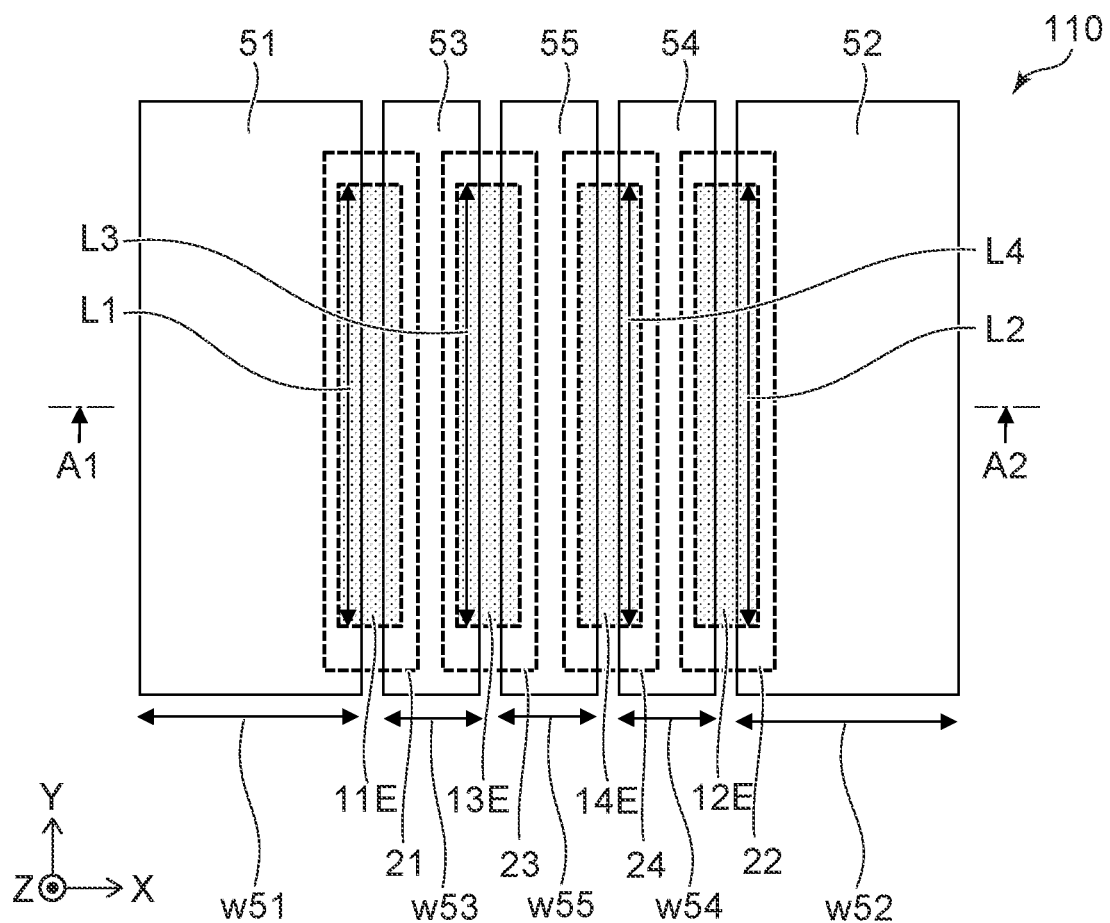
FIGS. 1A and 1B are schematic views illustrating a magnetic sensor according to a first embodiment.

According to one embodiment, a magnetic sensor includes a first magnetic element, a second magnetic element, a third magnetic element located between the first magnetic element and the second magnetic element in a first direction, a fourth magnetic element located between the third magnetic element and the second magnetic element in the first direction, a first conductive member, a second conductive member, a third conductive member located between the first conductive member and the second conductive member in the first direction, a fourth conductive member located between the third conductive member and the second conductive member in the first direction, a first magnetic member, a second magnetic member, a third magnetic member located between the first magnetic member and the second magnetic member in the first direction, a fourth magnetic member located between the third magnetic member and the second magnetic member in the first direction, and a fifth magnetic member located between the third magnetic member and the fourth magnetic member in the first direction. The first magnetic element and the first conductive member overlap a region between the first magnetic member and the third magnetic member in a second direction crossing the first direction. The second magnetic element and the second conductive member overlap a region between the fourth magnetic member and the second magnetic member in the second direction. The third magnetic element and the third conductive member overlap a region between the third magnetic member and the fifth magnetic member in the second direction. The fourth magnetic element and the fourth conductive member overlap a region between the fifth magnetic member and the fourth magnetic member in the second direction.

According to one embodiment, an inspection device includes the magnetic sensor described above, and a processor configured to process a signal output from the magnetic sensor.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1B:
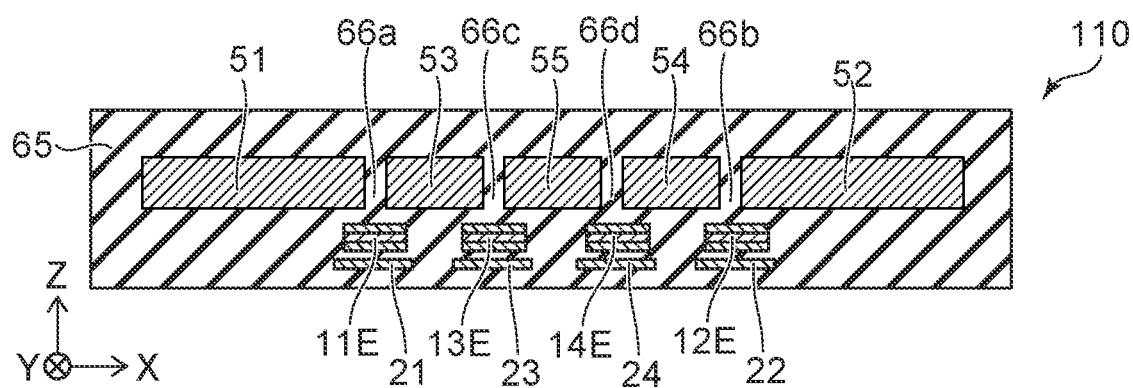

FIGS. 1A and 1B are schematic views illustrating a magnetic sensor according to a first embodiment.

Figure 2A:
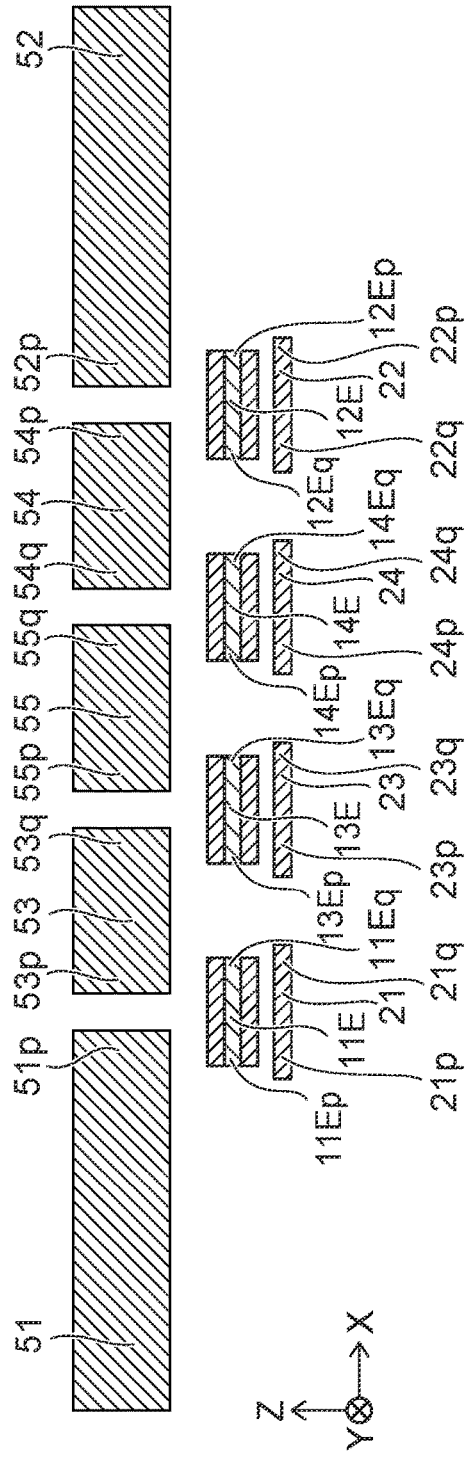
FIGS. 2A and 2B are schematic cross-sectional views illustrating the magnetic sensor according to the first embodiment.
Figure 2B:
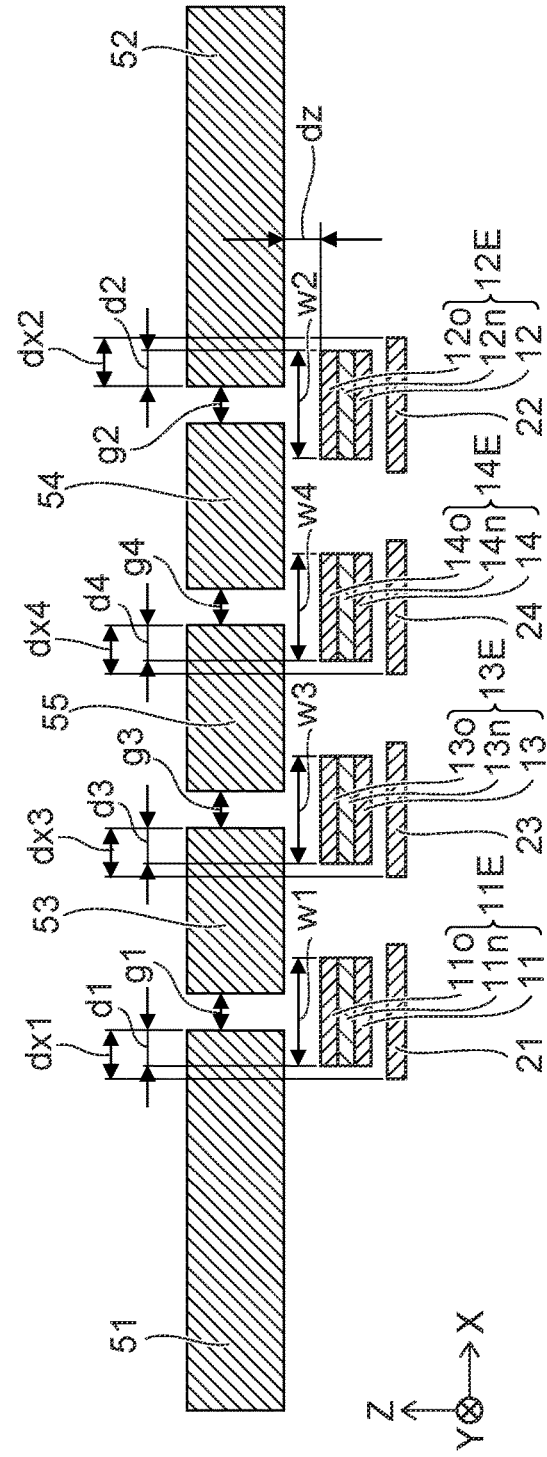

FIGS. 2A and 2B are schematic cross-sectional views illustrating the magnetic sensor according to the first embodiment.

FIG. 1A is a plan view. FIG. 1B and FIGS. 2A and 2B are line A1-A2 cross-sectional views of FIG. 1A. Some of the components are not illustrated in FIG. 1A and FIGS. 2A and 2B for easier viewing of the drawings.

As shown in FIGS. 1A and 1B, the magnetic sensor 110 according to the embodiment includes first to fourth magnetic elements 11E to 14E, first to fourth conductive members 21 to 24, and first to fifth magnetic members 51 to 55.

The third magnetic element 13E is located between the first magnetic element 11E and the second magnetic element 12E in a first direction. The fourth magnetic element 14E is located between the third magnetic element 13E and the second magnetic element 12E in the first direction.

The first direction is taken as an X-axis direction. One direction perpendicular to the X-axis direction is taken as a Z-axis direction. A direction perpendicular to the X-axis direction and the Z-axis direction is taken as a Y-axis direction.

The third conductive member 23 is located between the first conductive member 21 and the second conductive member 22 in the first direction (the X-axis direction). The fourth conductive member 24 is located between the third conductive member 23 and the second conductive member 22 in the first direction.

The third magnetic member 53 is located between the first magnetic member 51 and the second magnetic member 52 in the first direction (the X-axis direction). The fourth magnetic member 54 is located between the third magnetic member 53 and the second magnetic member 52 in the first direction. The fifth magnetic member 55 is located between the third magnetic member 53 and the fourth magnetic member 54 in the first direction.

As shown in FIG. 1B, the first magnetic element 11E and the first conductive member 21 overlap a region 66a between the first magnetic member 51 and the third magnetic member 53 in a second direction. The second direction crosses the first direction. The second direction is, for example, the Z-axis direction. The second magnetic element 12E and the second conductive member 22 overlap a region 66b between the fourth magnetic member 54 and the second magnetic member 52 in the second direction (e.g., the Z-axis direction). The third magnetic element 13E and the third conductive member 23 overlap a region 66c between the third magnetic member 53 and the fifth magnetic member 55 in the second direction. The fourth magnetic element 14E and the fourth conductive member 24 overlap a region 66d between the fifth magnetic member 55 and the fourth magnetic member 54 in the second direction.

In the example as shown in FIG. 1B, the magnetic sensor 110 includes an insulating member 65. The insulating member 65 is located around the first to fourth magnetic elements 11E to 14E, the first to fourth conductive members 21 to 24, and the first to fifth magnetic members 51 to 55. The regions 66a to 66d are, for example, portions of the insulating member 65. The insulating member 65 is not illustrated in FIG. 1A.

As shown in FIG. 2A, a portion 11Ep of the first magnetic element 11E and a portion 21p of the first conductive member 21 overlap at least a portion 51p of the first magnetic member 51 in the second direction (the Z-axis direction). Another portion 11Eq of the first magnetic element 11E and another portion 21q of the first conductive member 21 overlap a portion 53p of the third magnetic member 53 in the second direction.

A portion 12Ep of the second magnetic element 12E and a portion 22p of the second conductive member 22 overlap at least a portion 52p of the second magnetic member 52 in the second direction. Another portion 12Eq of the second magnetic element 12E and another portion 22q of the second conductive member 22 overlap a portion 54p of the fourth magnetic member 54 in the second direction.

A portion 13Ep of the third magnetic element 13E and a portion 23p of the third conductive member 23 overlap another portion 53q of the third magnetic member 53 in the second direction. Another portion 13Eq of the third magnetic element 13E and another portion 23q of the third conductive member 23 overlap a portion 55p of the fifth magnetic member 55 in the second direction.

A portion 14Ep of the fourth magnetic element 14E and a portion 24p of the fourth conductive member 24 overlap another portion 55q of the fifth magnetic member 55 in the second direction. Another portion 14Eq of the fourth magnetic element 14E and another portion 24q of the fourth conductive member 24 overlap another portion 54q of the fourth magnetic member 54 in the second direction.

In the example, at least a portion of the first magnetic element 11E is between the first conductive member 21 and the first magnetic member 51. At least a portion of the second magnetic element 12E is between the second conductive member 22 and the second magnetic member 52. At least a portion of the third magnetic element 13E is between the third conductive member 23 and the third magnetic member 53. At least a portion of the fourth magnetic element 14E is between the fourth conductive member 24 and the fourth magnetic member 54.

According to the embodiment, a magnetic field of a detection object (e.g., an external magnetic field) is concentrated by the first to fifth magnetic members 51 to 55. The concentrated magnetic field is efficiently applied to the first to fourth magnetic elements 11E to 14E. Thereby, the magnetic field of the detection object can be detected with high sensitivity. As described below, a current is supplied to the first to fourth conductive members 21 to 24. A magnetic field that is generated by the current flowing in the first to fourth conductive members 21 to 24 passes through the first to fifth magnetic members 51 to 55 and is efficiently applied to the first to fourth magnetic elements 11E to 14E. Higher sensitivity is obtained. For example, the current that is supplied to the conductive member can be reduced. For example, the power consumption can be reduced. For example, current leakage toward the magnetic elements due to capacitive coupling can be suppressed. According to the embodiment, a magnetic sensor can be provided in which the sensitivity can be increased. For example, the first to fifth magnetic members 51 to 55 function as a MFC (Magnetic Flux Concentrator).

The electrical resistances of the first to fourth magnetic elements 11E to 14E change according to the magnetic field of the detection object (e.g., the external magnetic field). This is caused by the orientation of the magnetization of the magnetic layer included in the magnetic element changing according to the magnetic field of the detection object.

As shown in FIG. 2B, the first magnetic element 11E includes a first magnetic layer 11, a first counter magnetic layer 110, and a first nonmagnetic layer 11n located between the first magnetic layer 11 and the first counter magnetic layer 110. The direction from the first magnetic layer 11 toward the first counter magnetic layer 110 is along the second direction (e.g., the Z-axis direction). The second magnetic element 12E includes a second magnetic layer 12, a second counter magnetic layer 120, and a second nonmagnetic layer 12n located between the second magnetic layer 12 and the second counter magnetic layer 120. The direction from the second magnetic layer 12 toward the second counter magnetic layer 120 is along the second direction. The third magnetic element 13E includes a third magnetic layer 13, a third counter magnetic layer 130, and a third nonmagnetic layer 13n located between the third magnetic layer 13 and the third counter magnetic layer 130. The direction from the third magnetic layer 13 toward the third counter magnetic layer 130 is along the second direction. The fourth magnetic element 14E includes a fourth magnetic layer 14, a fourth counter magnetic layer 140, and a fourth nonmagnetic layer 14n located between the fourth magnetic layer 14 and the fourth counter magnetic layer 140. The direction from the fourth magnetic layer 14 toward the fourth counter magnetic layer 140 is along the second direction.

For example, at least one of the orientation of the magnetization of the first magnetic layer 11 or the orientation of the magnetization of the first counter magnetic layer 110 changes according to the applied magnetic field. For example, at least one of the orientation of the magnetization of the second magnetic layer 12 or the orientation of the magnetization of the second counter magnetic layer 120 changes according to the applied magnetic field. For example, at least one of the orientation of the magnetization of the third magnetic layer 13 or the orientation of the magnetization of the third counter magnetic layer 130 changes according to the applied magnetic field. For example, at least one of the orientation of the magnetization of the fourth magnetic layer 14 or the orientation of the magnetization of the fourth counter magnetic layer 140 changes according to the applied magnetic field. The electrical resistance of each of the multiple magnetic elements changes according to the change of the angle between the magnetizations of two magnetic layers in each of the multiple magnetic elements.

In one example, the first to fourth nonmagnetic layers 11n to 14n include at least one selected from the group consisting of Cu, Ag, and Au. The magnetic element is, for example, a GMR (Giant Magnetic Resistance) element.

In one example, the first to fourth nonmagnetic layers 11n to 14n are insulative. The first to fourth nonmagnetic layers 11n to 14n include, for example, MgO, etc. The magnetic element may be, for example, a TMR (Tunnel Magneto Resistance) element.

As shown in FIG. 2B, the first magnetic element 11E has a width w1 along the first direction (the X-axis direction). The second magnetic element 12E has a width w2 along the first direction (the X-axis direction). The third magnetic element 13E has a width w3 along the first direction (the X-axis direction). The fourth magnetic element 14E has a width w4 along the first direction (the X-axis direction).

As shown in FIG. 1A, the first magnetic element 11E has a length L1 along a third direction. The third direction crosses a plane including the first and second directions. The third direction is, for example, the Y-axis direction. The second magnetic element 12E has a length L2 along the third direction. The third magnetic element 13E has a length L3 along the third direction. The fourth magnetic element 14E has a length L4 along the third direction.

The length L1 is greater than the width w1. The length L2 is greater than the width w2. The length L3 is greater than the width w3. The length L4 is greater than the width w4. For example, a stable magnetization is obtained in the magnetic layer included in the magnetic element.

Figure 3:
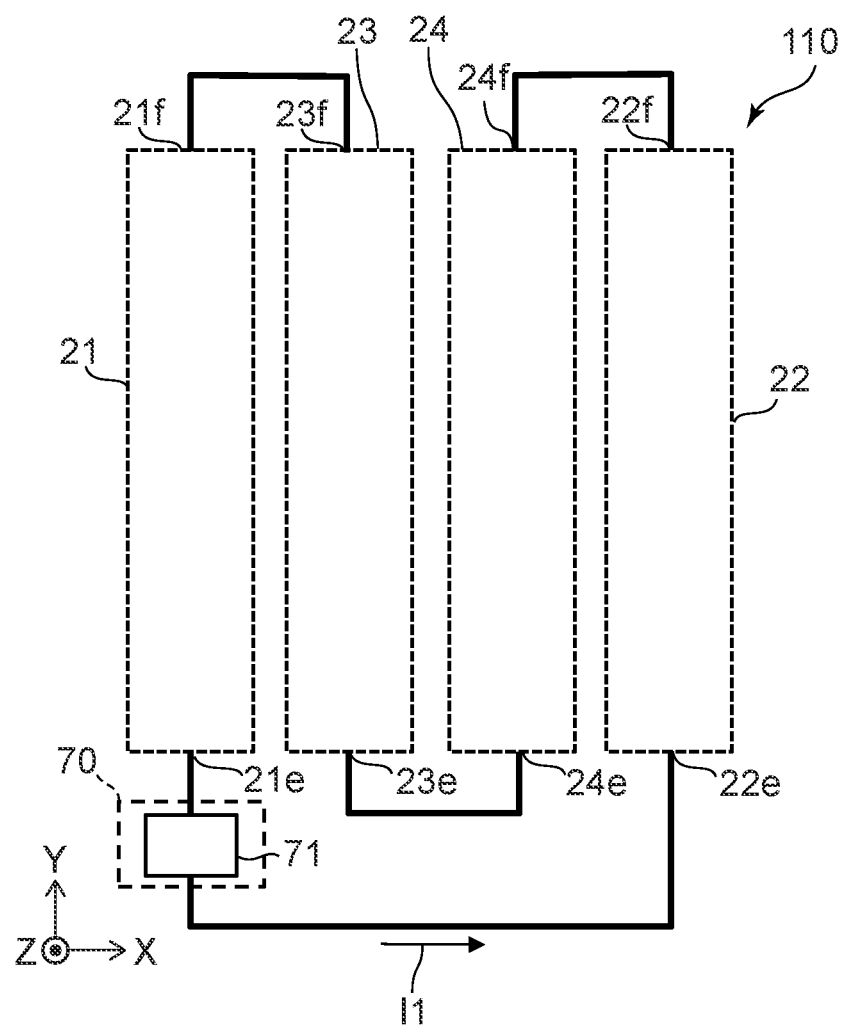
FIG. 3 is a schematic plan view illustrating the magnetic sensor according to the first embodiment.

FIG. 3 is a schematic plan view illustrating the magnetic sensor according to the first embodiment.

As shown in FIG. 3, the magnetic sensor 110 may include a first circuit 71. The first circuit 71 is configured to supply a first current I1 that includes an alternating current component to the first to fourth conductive members 21 to 24. For example, the first circuit 71 may be included in a controller 70.

As shown in FIG. 3, the direction from one end 21e of the first conductive member 21 toward another end 21f of the first conductive member 21 is along the third direction. As described above, the third direction crosses a plane including the first and second directions. The third direction is, for example, the Y-axis direction. The direction from one end 22e of the second conductive member 22 toward another end 22f of the second conductive member 22 is along the third direction. The direction from one end 23e of the third conductive member 23 toward another end 23f of the third conductive member 23 is along the third direction. The direction from one end 24e of the fourth conductive member 24 toward another end 24f of the fourth conductive member 24 is along the third direction.

In the example, the other end 21f of the first conductive member 21 is electrically connected with the other end 23f of the third conductive member 23. The one end 23e of the third conductive member 23 is electrically connected with the one end 24e of the fourth conductive member 24. The other end 24f of the fourth conductive member 24 is electrically connected with the other end 22f of the second conductive member 22.

The first circuit 71 is configured to supply the first current I1 that includes the alternating current component between the one end 21e of the first conductive member 21 and the one end 22e of the second conductive member 22. As described below, a magnetic field that is generated by the first current I1 including the alternating current component is applied to the magnetic elements detection with higher sensitivity is possible thereby.

Figure 4:
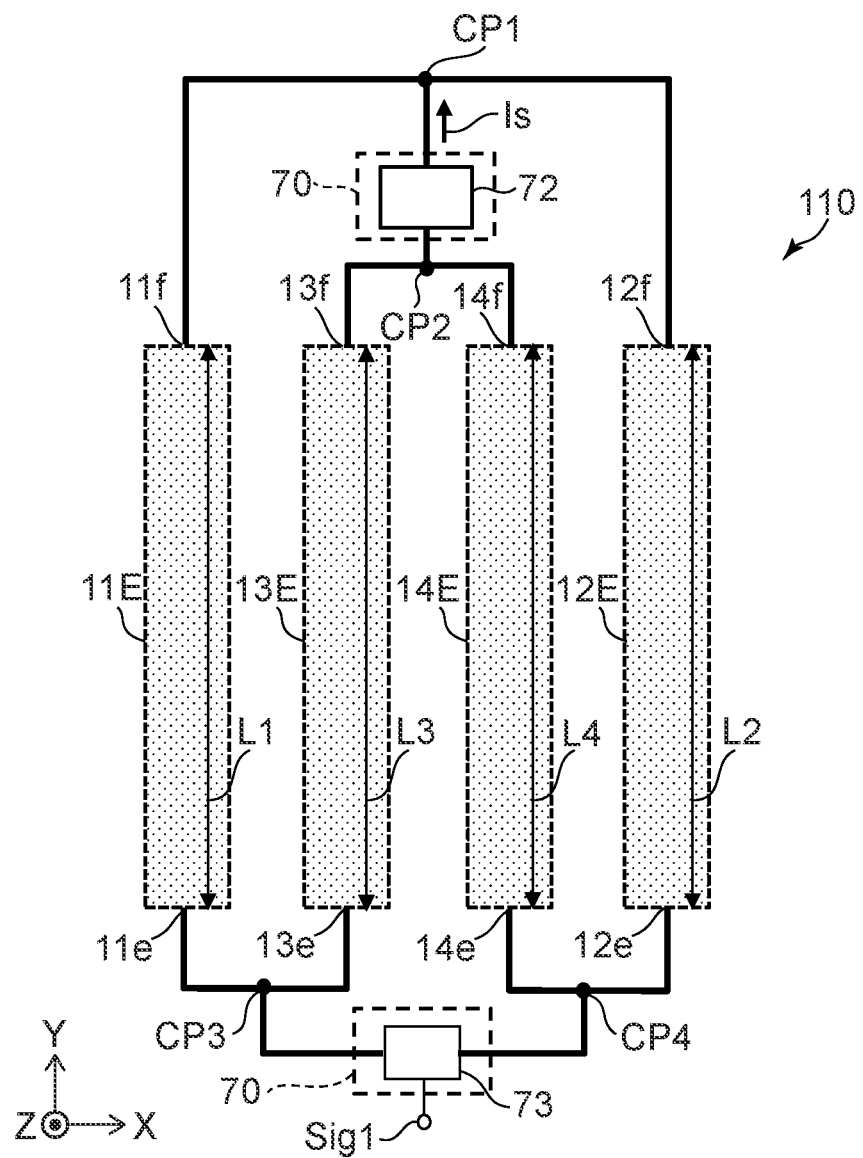
FIG. 4 is a schematic plan view illustrating the magnetic sensor according to the first embodiment.

FIG. 4 is a schematic plan view illustrating the magnetic sensor according to the first embodiment.

As shown in FIG. 4, the magnetic sensor 110 may include a second circuit 72. The second circuit 72 is configured to supply a detection current Is to the first to fourth magnetic elements 11E to 14E. For example, the second circuit 72 may be included in the controller 70.

As shown in FIG. 4, the direction from one end 11e of the first magnetic element 11E toward another end 11f of the first magnetic element 11E is along the third direction (e.g., the Y-axis direction). The direction from one end 12e of the second magnetic element 12E toward another end 12f of the second magnetic element 12E is along the third direction. The direction from one end 13e of the third magnetic element 13E toward another end 13f of the third magnetic element 13E is along the third direction. The direction from one end 14e of the fourth magnetic element 14E toward another end 14f of the fourth magnetic element 14E is along the third direction.

In the example, the other end 11f of the first magnetic element 11E is electrically connected with the other end 12f of the second magnetic element 12E. The one end 11e of the first magnetic element 11E is electrically connected with the one end 13e of the third magnetic element 13E. The other end 13f of the third magnetic element 13E is electrically connected with the other end 14f of the fourth magnetic element 14E. The one end 14e of the fourth magnetic element 14E is electrically connected with the one end 12e of the second magnetic element 12E. The second circuit 72 is configured to supply the detection current Is between a first connection point CP1 and a second connection point CP2, in which the first connection point CP1 is between the other end 11f of the first magnetic element 11E and the other end 12f of the second magnetic element 12E, and the second connection point CP2 is between the other end 13f of the third magnetic element 13E and the other end 14f of the fourth magnetic element 14E.

As shown in FIG. 4, the magnetic sensor 110 may further include a third circuit 73. For example, the third circuit 73 may be included in the controller 70.

The third circuit 73 is configured to detect the change of the potential between a third connection point CP3 and a fourth connection point CP4, in which the third connection point CP3 is between the one end 11e of the first magnetic element 11E and the one end 13e of the third magnetic element 13E, and the fourth connection point CP4 is between the one end 14e of the fourth magnetic element 14E and the one end 12e of the second magnetic element 12E. The third circuit 73 is configured to output a signal Sig1 that corresponds to the change of the potential. The third connection point CP3 and the fourth connection point CP4 correspond to two midpoints of a bridge circuit.

An example of the change of the electrical resistance of the first magnetic element 11E when the current flows in the first conductive member 21 will now be described. The description of the example of the change of the electrical resistance of the first magnetic element 11E also is applicable to the other magnetic elements.

Figure 5A:
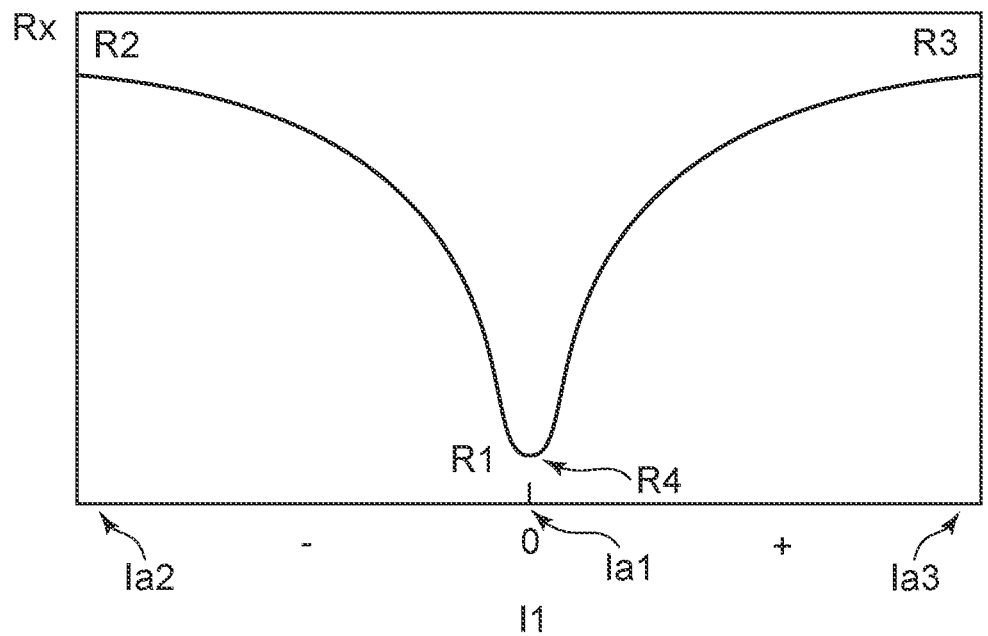
FIGS. 5A and 5B are schematic views illustrating characteristics of the magnetic sensor according to the first embodiment.
Figure 5B:
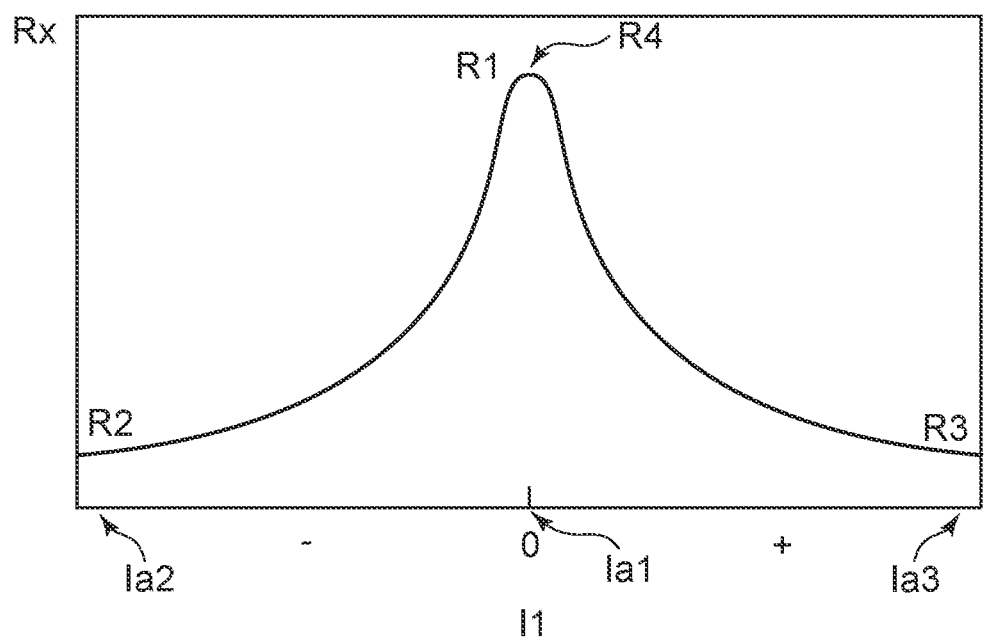

FIGS. 5A and 5B are schematic views illustrating characteristics of the magnetic sensor according to the first embodiment.

In these figures, the horizontal axis corresponds to the value of the current (e.g., the first current I1) flowing in the first conductive member 21. The vertical axis is an electrical resistance Rx of the first magnetic element 11E. According to the embodiment as shown in FIGS. 5A and 5B, the electrical resistance Rx has an even-function characteristic with respect to the change of the current (the first current I1).

For example, the electrical resistance Rx of the first magnetic element 11E has a first value R1 when a first-value current Ia1 is supplied to the first conductive member 21. The electrical resistance Rx has a second value R2 when a second-value current Ia2 is supplied to the first conductive member 21. The electrical resistance Rx has a third value R3 when a third-value current Ia3 is supplied to the first conductive member 21. The absolute value of the first-value current Ia1 is less than the absolute value of the second-value current Ia2 and less than the absolute value of the third-value current Ia3. For example, the first-value current Ia1 may be substantially 0. The orientation of the second-value current Ia2 is opposite to the orientation of the third-value current Ia3.

In the example of FIG. 5A, the first value R1 is less than the second value R2 and less than the third value R3. In the example of FIG. 5A, the electrical resistance Rx has a "valley-like" characteristic. The first value R1 is, for example, the minimum value of the electrical resistance. In the example of FIG. 5B, the first value R1 is greater than the second value R2 and greater than the third value R3. In the example of FIG. 5B, the electrical resistance Rx has a "hill-like" characteristic. The first value R1 is, for example, the maximum value of the electrical resistance.

For example, when the external magnetic field is substantially 0, the magnetization of the first magnetic layer 11 and the magnetization of the first counter magnetic layer 110 have "parallel alignment"; for example, a "valley-like" characteristic is obtained due to the action of interlayer magnetic coupling. In such a case, for example, the thickness of the first nonmagnetic layer 11n is not less than 2.5 nm. For example, when the external magnetic field is substantially 0, the magnetization of the first magnetic layer 11 and the magnetization of the first counter magnetic layer 110 have "antiparallel alignment"; for example, a "hill-like" characteristic is obtained due to the action of interlayer magnetic coupling. In such a case, the thickness of the first nonmagnetic layer 11n is, for example, not less than 1.9 nm and not more than 2.1 nm.

For example, when a current does not flow in the first conductive member 21, the electrical resistance Rx has a fourth value R4. For example, the first value R1 is substantially equal to the fourth value R4 when the current does not flow. For example, the ratio of the absolute value of the difference between the first value R1 and the fourth value R4 to the fourth value R4 is not more than 0.01. The ratio may be not more than 0.001. A substantially even-function characteristic with respect to the positive and negative current is obtained.

Such a relationship between the first current I1 and the electrical resistance Rx is based on the magnetic field due to the first current I1 being applied to the first magnetic element 11E and based on the electrical resistance Rx of the first magnetic element 11E changing according to the intensity of the magnetic field.

Similarly to the example shown in FIG. 5A or FIG. 5B, the electrical resistance Rx when an external magnetic field is applied to the first magnetic element 11E also has an even-function characteristic. The external magnetic field includes, for example, a component along the X-axis direction.

Figure 6A:
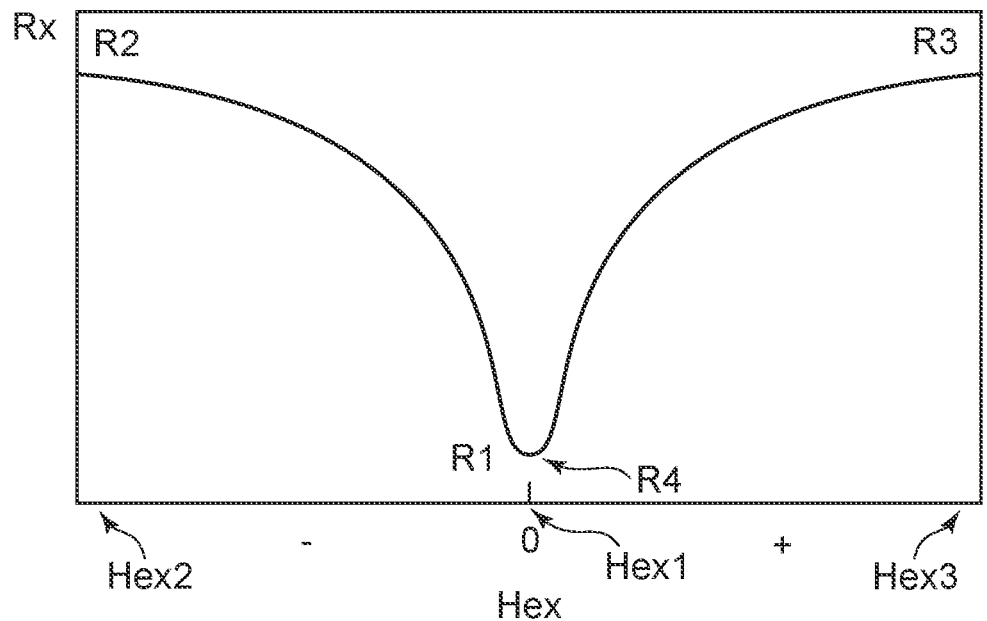
FIGS. 6A and 6B are schematic views illustrating characteristics of the magnetic sensor according to the first embodiment.
Figure 6B:
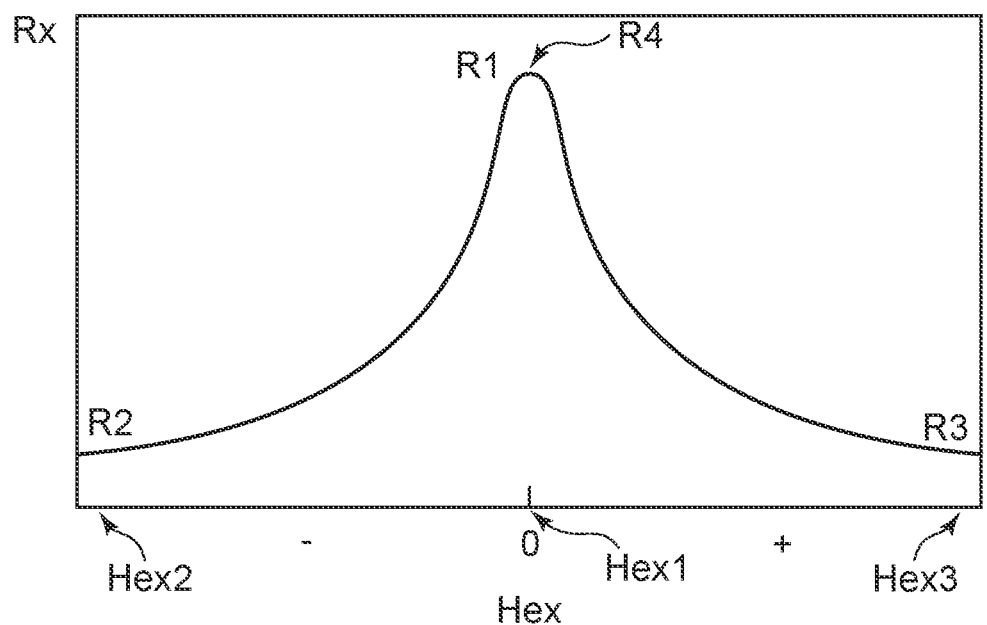

FIGS. 6A and 6B are schematic views illustrating characteristics of the magnetic sensor according to the first embodiment.

In these figures, the horizontal axis is the intensity of an external magnetic field Hex applied to the first magnetic element 11E. The vertical axis is the electrical resistance Rx of the first magnetic element 11E. These figures correspond to the R-H characteristic. As shown in FIGS. 6A and 6B, the electrical resistance Rx has an even-function characteristic with respect to the magnetic field (the external magnetic field Hex, e.g., the magnetic field in the X-axis direction) that is applied to the first magnetic element 11E.

As shown in FIGS. 6A and 6B, the electrical resistance Rx of the first magnetic element 11E has the first value R1 when a first magnetic field Hex1 is applied to the first magnetic element 11E. The electrical resistance Rx has a second value R2 when a second magnetic field Hex2 is applied to the first magnetic element 11E. The electrical resistance Rx has a third value R3 when a third magnetic field Hex3 is applied to the first magnetic element 11E. The absolute value of the first magnetic field Hex1 is less than the absolute value of the second magnetic field Hex2 and less than the absolute value of the third magnetic field Hex3. The orientation of the second magnetic field Hex2 is opposite to the orientation of the third magnetic field Hex3.

In the example of FIG. 6A, the first value R1 is less than the second value R2 and less than the third value R3. In the example of FIG. 6B, the first value R1 is greater than the second value R2 and greater than the third value R3. For example, the electrical resistance Rx has the fourth value R4 when the external magnetic field is not applied to the first magnetic element 11E. The first value R1 is substantially equal to the fourth value R4 when the external magnetic field is not applied. For example, the ratio of the absolute value of the difference between the first value R1 and the fourth value R4 to the fourth value R4 is not more than 0.01. The ratio may be not more than 0.001. A substantially even-function characteristic is obtained for the positive and negative external magnetic fields.

By utilizing such an even-function characteristic, highly-sensitive detection is possible as follows.

An example will now be described in which the first current I1 is an alternating current and substantially does not include a direct current component. The first current I1 (the alternating current) is supplied to the first conductive member 21; and an alternating current magnetic field due to the alternating current is applied to the first magnetic element 11E. An example of the change of the electrical resistance Rx at this time will now be described.

Figure 7A:
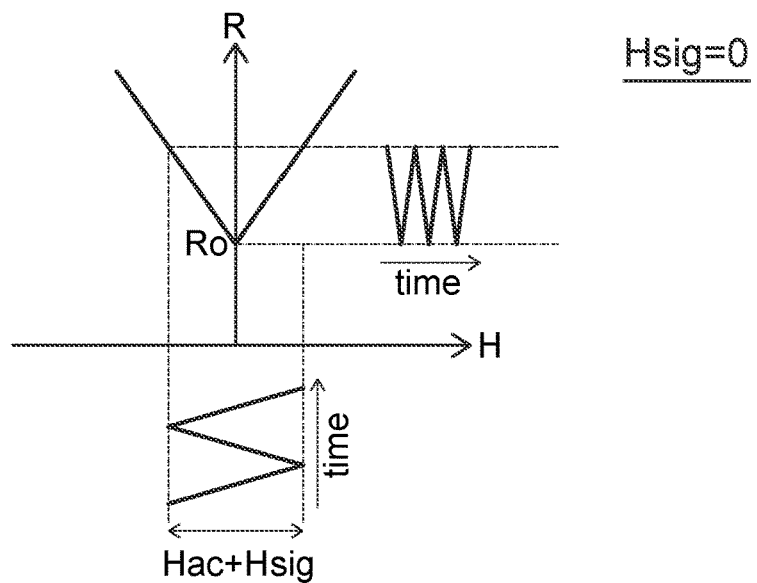
FIGS. 7A to 7C are graphs illustrating characteristics of the magnetic sensor according to the first embodiment.
Figure 7B:
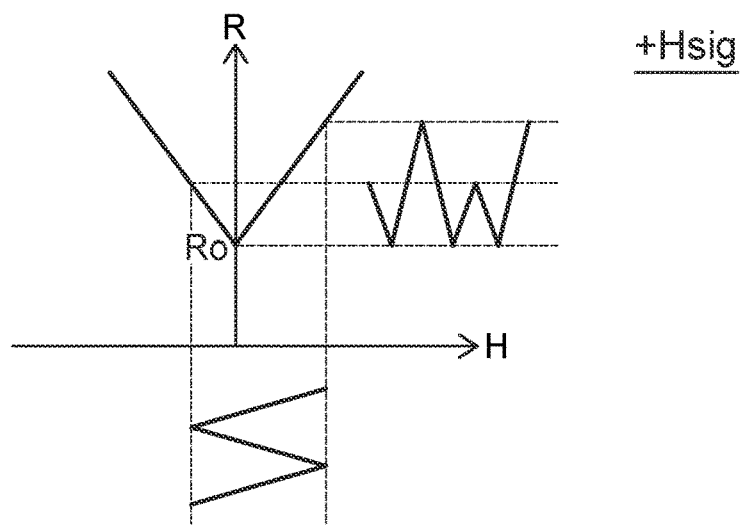
Figure 7C:
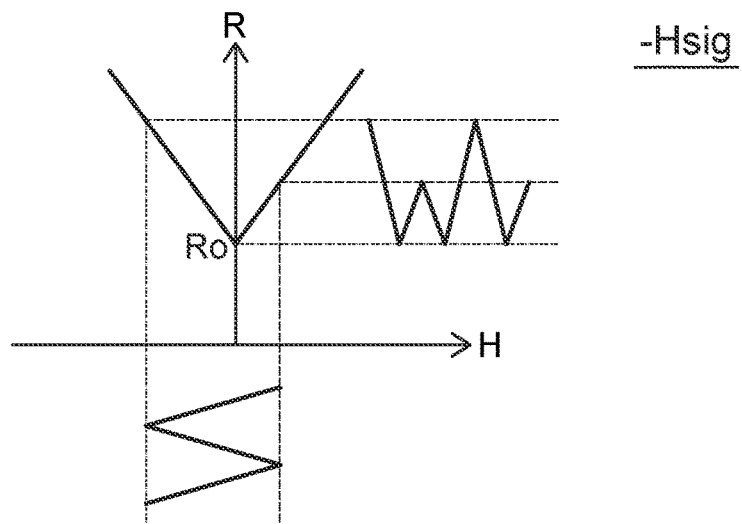

FIGS. 7A to 7C are graphs illustrating characteristics of the magnetic sensor according to the first embodiment.

FIG. 7A shows characteristics when a signal magnetic field Hsig (an external magnetic field) applied to the first magnetic element 11E is 0. FIG. 7B shows characteristics when the signal magnetic field Hsig is positive. FIG. 7C shows characteristics when the signal magnetic field Hsig is negative. These figures show the relationship between a magnetic field H and a resistance R (corresponding to the electrical resistance Rx).

As shown in FIG. 7A, when the signal magnetic field Hsig is 0, the resistance R has a characteristic that is symmetric with respect to the positive and negative magnetic field H. When an alternating current magnetic field Hac is zero, the resistance R is a low resistance Ro. For example, the magnetization of the free magnetic layer is rotated substantially identically to the positive and negative magnetic field H. Therefore, a symmetric resistance change is obtained. The change of the resistance R with respect to the alternating current magnetic field Hac has the same value between the positive and negative polarities. The period of the change of the resistance R is ½ times the period of the alternating current magnetic field Hac. The change of the resistance R substantially does not include the frequency component of the alternating current magnetic field Hac.

As shown in FIG. 7B, the characteristic of the resistance R shifts to the positive magnetic field H side when a positive signal magnetic field Hsig is applied. For example, the resistance R becomes high for the alternating current magnetic field Hac on the positive side. The resistance R becomes small for the alternating current magnetic field Hac on the negative side.

As shown in FIG. 7C, the characteristic of the resistance R shifts to the negative magnetic field H side when a negative signal magnetic field Hsig is applied. For example, the resistance R becomes low for the alternating current magnetic field Hac on the positive side. The resistance R becomes large for the alternating current magnetic field Hac on the negative side.

Change in the resistance R is different for the positive and negative of the alternating current magnetic field Hac when a signal magnetic field Hsig with non-zero magnitude is applied. The period of the change of the resistance R with respect to the positive and negative of the alternating current magnetic field Hac is equal to the period of the alternating current magnetic field Hac. An output voltage that has an alternating current frequency component corresponding to the signal magnetic field Hsig is generated.

The characteristics described above are obtained in the case where the signal magnetic field Hsig does not temporally change. The case where the signal magnetic field Hsig temporally changes is as follows. The frequency of the signal magnetic field Hsig is taken as a signal frequency fsig. The frequency of the alternating current magnetic field Hac is taken as an alternating current frequency fac. In such a case, an output that corresponds to the signal magnetic field Hsig is generated at the frequency of fac±fsig.

In the case where the signal magnetic field Hsig temporally changes, the signal frequency fsig is, for example, not more than 1 kHz. On the other hand, the alternating current frequency fac is sufficiently greater than the signal frequency fsig. For example, the alternating current frequency fac is not less than 10 times the signal frequency fsig.

For example, the signal magnetic field Hsig can be detected with high accuracy by extracting an output voltage having the same period (frequency) component (alternating current frequency component) as the period (the frequency) of the alternating current magnetic field Hac. In the magnetic sensor 111 according to the embodiment, the external magnetic field Hex (the signal magnetic field Hsig) that is the detection object can be detected with high sensitivity by utilizing such characteristics. According to the embodiment, the external magnetic field Hex (the signal magnetic field Hsig) and the alternating current magnetic field Hac due to the first current I1 can be efficiently applied to the first magnetic element 11E by the first and second magnetic members 51 and 52. High sensitivity is obtained.

For example, the phase of the magnetic field that is applied to the first magnetic element 11E by the first current I1 supplied to the first conductive member 21 is opposite to the phase of the magnetic field that is applied to the third magnetic element 13E by the first current I1 supplied to the third conductive member 23. For example, the phase of the magnetic field that is applied to the second magnetic element 12E by the first current I1 supplied to the second conductive member 22 is opposite to the phase of the magnetic field that is applied to the fourth magnetic element 14E by the first current I1 supplied to the fourth conductive member 24. For example, the phase of the magnetic field that is applied to the first magnetic element 11E by the first current I1 supplied to the first conductive member 21 is opposite to the phase of the magnetic field that is applied to the second magnetic element 12E by the first current I1 supplied to the second conductive member 22. By such a bridge circuit, the noise component is suppressed, and higher sensitivity is obtained.

According to the embodiment as described below, the configuration of the first magnetic member 51 may be different from the configurations of the third to fifth magnetic members 53 to 55. The configuration of the second magnetic member 52 may be different from the configuration of the third to fifth magnetic members 53 to 55. Thereby, a more uniform magnetic field can be applied to the four magnetic elements. Higher sensitivity is obtained. Compared to the other portions, it was found that the magnetic field is weak between the first magnetic member 51 and the third magnetic member 53 and between the fourth magnetic member 54 and the second magnetic member 52. A more uniform magnetic field is obtained by setting the configurations of the first and second magnetic members 51 and 52 to be different from the configurations of the other magnetic members.

For example, as shown in FIG. 1A, a first magnetic member width w51 along the first direction (the X-axis direction) of the first magnetic member 51 is greater than a fifth magnetic member width w55 along the first direction of the fifth magnetic member 55. A second magnetic member width w52 along the first direction (the X-axis direction) of the second magnetic member 52 is greater than the fifth magnetic member width w55. A third magnetic member width w53 along the first direction of the third magnetic member 53 is less than the first magnetic member width w51. A fourth magnetic member width w54 along the first direction of the fourth magnetic member 54 is less than the second magnetic member width w52. A more uniform magnetic field is obtained by such a configuration.

Figure 8:
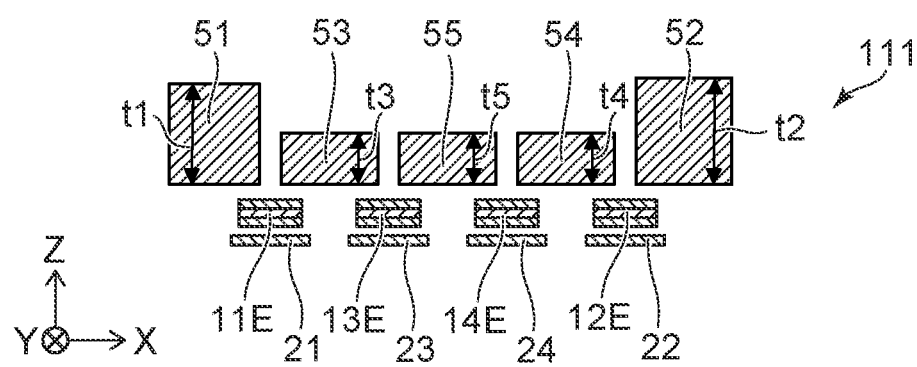
FIG. 8 is a schematic cross-sectional view illustrating a magnetic sensor according to the first embodiment.

FIG. 8 is a schematic cross-sectional view illustrating a magnetic sensor according to the first embodiment.

As shown in FIG. 8, the magnetic sensor 111 according to the embodiment also includes the first to fourth magnetic elements 11E to 14E, the first to fourth conductive members 21 to 24, and the first to fifth magnetic members 51 to 55. In the magnetic sensor 111, the thicknesses of the first to fifth magnetic members 51 to 55 are different from each other. Otherwise, the configuration of the magnetic sensor 111 may be similar to the magnetic sensor 110.

In the magnetic sensor 111, a first magnetic member thickness t1 along the second direction (the Z-axis direction) of the first magnetic member 51 is greater than a fifth magnetic member thickness t5 along the second direction of the fifth magnetic member 55. A second magnetic member thickness t2 along the second direction (the Z-axis direction) of the second magnetic member 52 is greater than the fifth magnetic member thickness t5. A third magnetic member thickness t3 along the second direction of the third magnetic member 53 is less than the first magnetic member thickness t1. A fourth magnetic member thickness t4 along the second direction of the fourth magnetic member 54 is less than the second magnetic member thickness t2. A more uniform magnetic field is obtained by such a configuration.

In the magnetic sensor 111 as shown in FIG. 8, the widths of the first to fifth magnetic members 51 to 55 may be equal to each other. In the magnetic sensor 111, similarly to the magnetic sensor 110, the widths of the first to fifth magnetic members 51 to 55 may be different from each other.

Figure 9A:
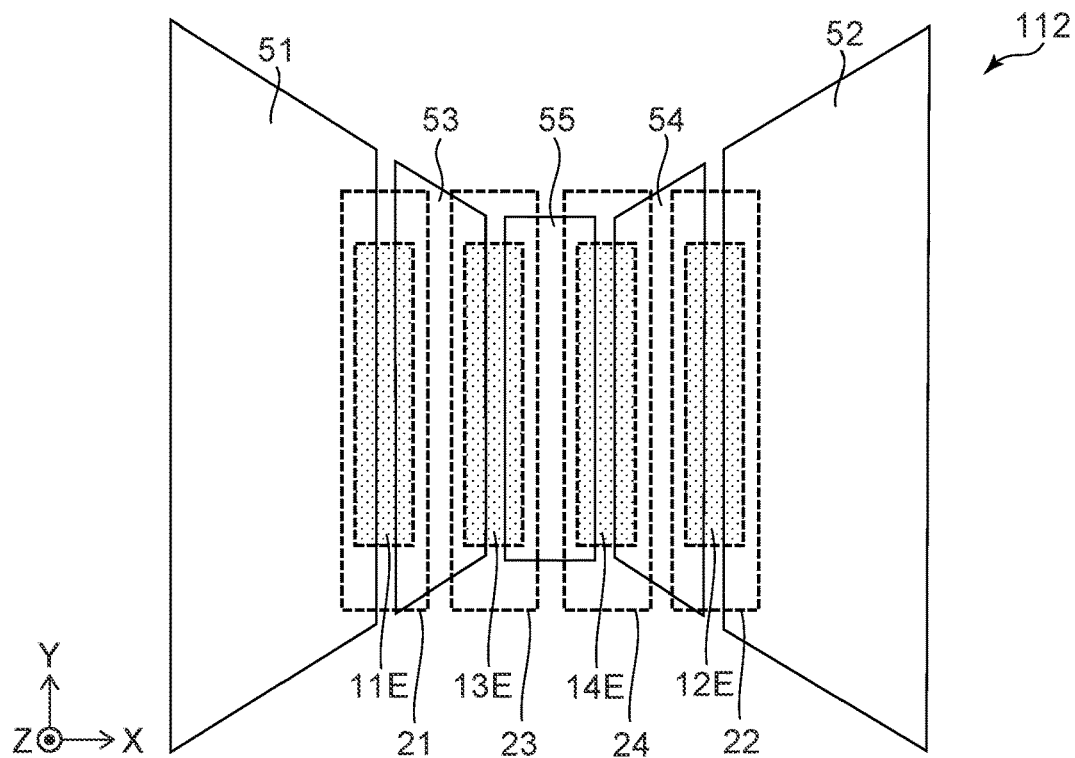
FIGS. 9A and 9B are schematic plan views illustrating a magnetic sensor according to the first embodiment.
Figure 9B:
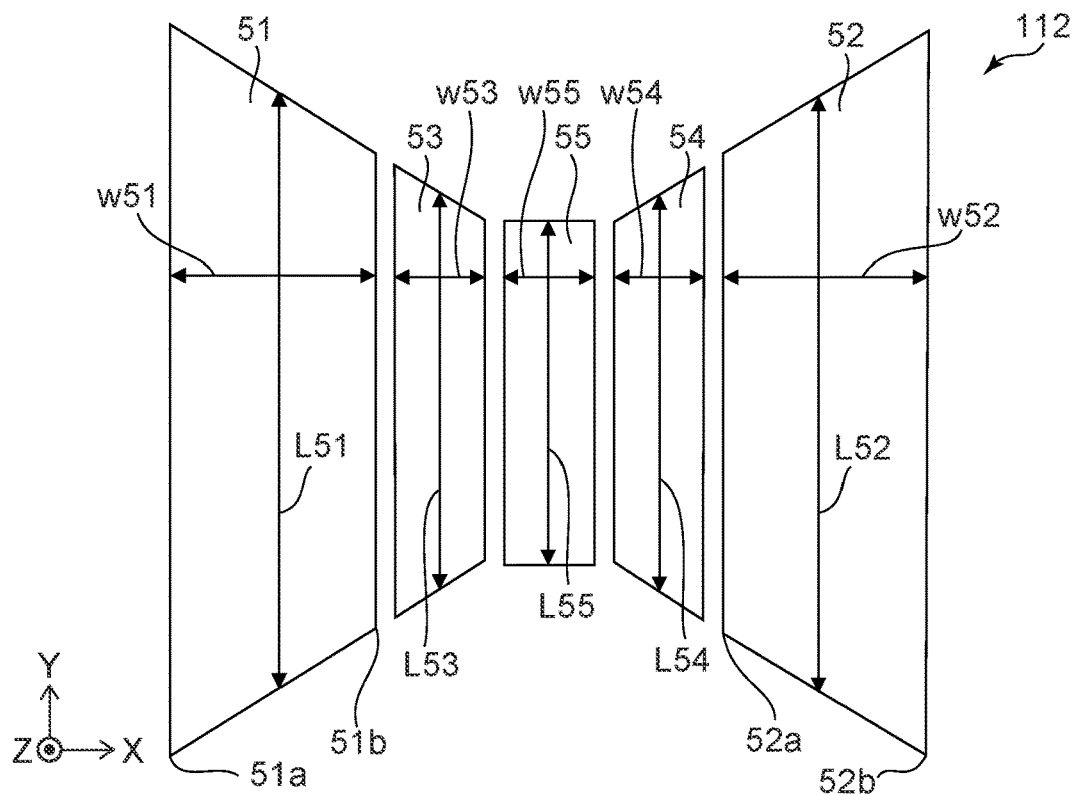

FIGS. 9A and 9B are schematic plan views illustrating a magnetic sensor according to the first embodiment.

As shown in FIG. 9A, the magnetic sensor 112 according to the embodiment also includes the first to fourth magnetic elements 11E to 14E, the first to fourth conductive members 21 to 24, and the first to fifth magnetic members 51 to 55. In the magnetic sensor 112, the lengths in the Y-axis direction of the first to fifth magnetic members 51 to 55 are different from each other. Otherwise, the configuration of the magnetic sensor 112 may be similar to the magnetic sensor 110.

As shown in FIG. 9B, a first magnetic member length L51 along the third direction (e.g., the Y-axis direction) of the first magnetic member 51 is greater than a fifth magnetic member length L55 along the third direction of the fifth magnetic member 55. A second magnetic member length L52 along the third direction (e.g., the Y-axis direction) of the second magnetic member 52 is greater than the fifth magnetic member length L55. A third magnetic member length L53 along the third direction of the third magnetic member 53 is less than the first magnetic member length L51. A fourth magnetic member length L54 along the third direction of the fourth magnetic member 54 is less than the second magnetic member length L52. A more uniform magnetic field is obtained by such a configuration. Practically, the lengths described above may be taken as the length in the third direction (the Y-axis direction) at the position of the center in the first direction (the X-axis direction) for each of the multiple magnetic members.

As shown in FIG. 9B, the length along the Y-axis direction of the first magnetic member 51 may change along the X-axis direction. For example, the first magnetic member 51 includes a first magnetic member end 51a and a first magnetic member other-end 51b. The first magnetic member other-end 51b is between the first magnetic member end 51a and the third magnetic member 53 in the first direction (the X-axis direction). The first magnetic member length L51 along the third direction (the Y-axis direction) of the first magnetic member 51 may increase in the orientation from the first magnetic member other-end 51b toward the first magnetic member end 51a.

For example, the second magnetic member 52 includes a second magnetic member end 52a and a second magnetic member other-end 52b. The second magnetic member end 52a is between the fourth magnetic member 54 and the second magnetic member other-end 52b In the first direction (the X-axis direction). The second magnetic member length L52 along the third direction (the Y-axis direction) of the second magnetic member 52 may increase in the orientation from the second magnetic member end 52a toward the second magnetic member other-end 52b. The length in the Y-axis direction may change along the X-axis direction for each of the third and fourth magnetic members 53 and 54.

Figure 10:
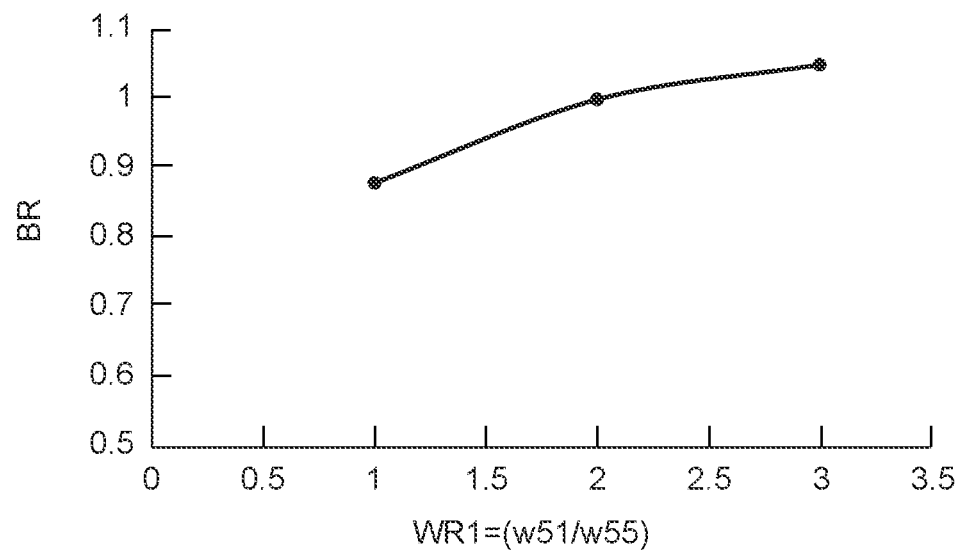
FIG. 10 is a graph illustrating a characteristic of the magnetic sensor.

FIG. 10 is a graph illustrating a characteristic of the magnetic sensor.

FIG. 10 illustrates simulation results of a characteristic when the first magnetic member width w51 along the first direction (the X-axis direction) of the first magnetic member 51 of the configuration of the magnetic sensor 110 is changed. In the simulation, the third magnetic member width w53 along the first direction of the third magnetic member 53 is equal to the fifth magnetic member width w55 along the first direction of the fifth magnetic member 55. The fourth magnetic member width w54 along the first direction of the fourth magnetic member 54 is equal to the fifth magnetic member width w55. The second magnetic member width w52 along the first direction of the second magnetic member 52 is equal to the first magnetic member width w51 along the first direction of the first magnetic member 51. The horizontal axis of FIG. 10 is a ratio WR1 of the first magnetic member width w51 to the fifth magnetic member width w55. The vertical axis is a ratio BR of the magnetic flux density at the position of the first magnetic element 11E to the magnetic flux density at the position of the second magnetic element 12E when the external magnetic field is applied. The magnetic flux density is uniform when the ratio BR is 1.

As shown in FIG. 10, the ratio BR is low and is about 0.85 when the ratio WR1 is 1 and the magnetic member widths are equal. The ratio BR is near 1 when the ratio WR1 is not less than 2 and not more than 3.

According to the embodiment, it is favorable for the ratio WR1 of the first magnetic member width w51 to the fifth magnetic member width w55 to be not less than 2 and not more than 3. A uniform magnetic field can be applied to the first to fourth magnetic elements 11E to 14E.

For example, the first magnetic member thickness t1 along the second direction (the Z-axis direction) of the first magnetic member 51 (referring to FIG. 8) is not less than 2 times and not more than 4 times 2 times the fifth magnetic member thickness t5 along the second direction of the fifth magnetic member 55.

For example, the first magnetic member length L51 along the third direction (e.g., the Y-axis direction) of the first magnetic member 51 (referring to FIG. 9B) is not less than 2 times and not more than 3 times the fifth magnetic member length L55 along the third direction of the fifth magnetic member 55.

Examples of the overlap amount between the first to fourth magnetic elements 11E to 14E and the magnetic members and the overlap amount between the first to fourth conductive members 21 to 24 and the magnetic members will now be described.

As shown in FIG. 2A, the portion 11Ep of the first magnetic element 11E overlaps the portion 51p of the first magnetic member 51 in the second direction (the Z-axis direction). As shown in FIG. 2B, the width along the first direction (the X-axis direction) of the portion 11Ep of the first magnetic element 11E is taken as a width d1. As shown in FIG. 2A, the other portion 11Eq of the first magnetic element 11E overlaps the portion 53p of the third magnetic member 53 in the second direction (the Z-axis direction). The width along the first direction (the X-axis direction) of the other portion 11Eq of the first magnetic element 11E is substantially equal to the width d1. As described above, the first magnetic element 11E has the width w1 along the first direction (referring to FIG. 2B). According to the embodiment, it is favorable for the ratio of the width d1 to the width w1 to be not less than 0.1 and not more than 0.4.

As shown in FIG. 2A, the portion 12Ep of the second magnetic element 12E overlaps the portion 52p of the second magnetic member 52 in the second direction (the Z-axis direction). As shown in FIG. 2B, a width along the first direction (the X-axis direction) of the portion 12Ep of the second magnetic element 12E is taken as a width d2. As shown in FIG. 2A, the other portion 12Eq of the second magnetic element 12E overlaps the portion 54p of the fourth magnetic member 54 in the second direction (the Z-axis direction). The width along the first direction (the X-axis direction) of the other portion 12Eq of the second magnetic element 12E is substantially equal to the width d2. As described above, the second magnetic element 12E has the width w2 along the first direction (referring to FIG. 2B). According to the embodiment, it is favorable for the ratio of the width d2 to the width w2 to be not less than 0.1 and not more than 0.4.

As shown in FIG. 2A, the portion 13Ep of the third magnetic element 13E overlaps the other portion 53q of the third magnetic member 53 in the second direction (the Z-axis direction). As shown in FIG. 2B, the width along the first direction (the X-axis direction) of the portion 13Ep of the third magnetic element 13E is taken as a width d3. As shown in FIG. 2A, the other portion 13Eq of the third magnetic element 13E overlaps the portion 55p of the fifth magnetic member 55 in the second direction (the Z-axis direction). The width along the first direction (the X-axis direction) of the other portion 13Eq of the third magnetic element 13E is substantially equal to the width d3. As described above, the third magnetic element 13E has the width w3 along the first direction (referring to FIG. 2B). According to the embodiment, it is favorable for the ratio of the width d3 to the width w3 to be not less than 0.1 and not more than 0.4.

As shown in FIG. 2A, the portion 14Ep of the fourth magnetic element 14E overlaps the other portion 55q of the fifth magnetic member 55 in the second direction (the Z-axis direction). As shown in FIG. 2B, the width along the first direction (the X-axis direction) of the portion 14Ep of the fourth magnetic element 14E is taken as a width d4. As shown in FIG. 2A, the other portion 14Eq of the fourth magnetic element 14E overlaps the other portion 54q of the fourth magnetic member 54 in the second direction (the Z-axis direction). The width along the first direction (the X-axis direction) of the other portion 14Eq of the fourth magnetic element 14E is substantially equal to the width d4. As described above, the fourth magnetic element 14E has the width w4 along the first direction (referring to FIG. 2B). According to the embodiment, it is favorable for the ratio of the width d4 to the width w4 to be not less than 0.1 and not more than 0.4.

By such a configuration, the magnetic field that is concentrated by the magnetic members is more efficiently applied to the magnetic elements.

Figure 11:
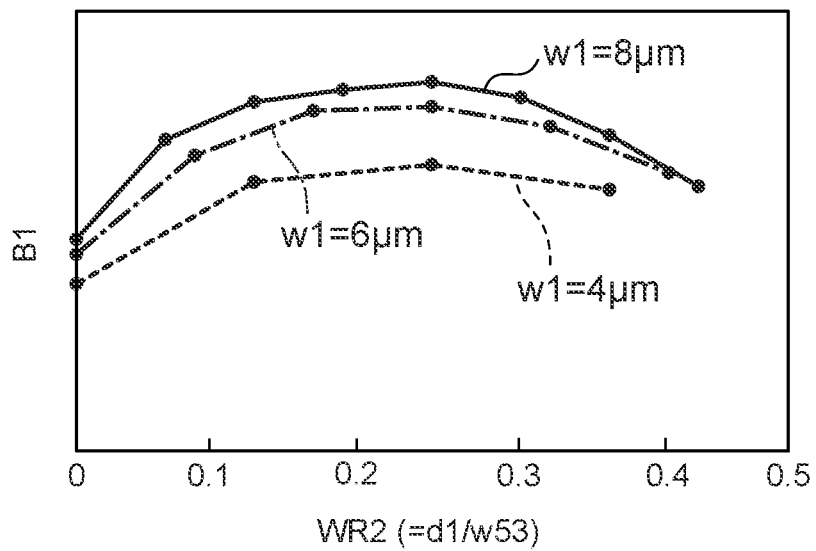
FIG. 11 is a graph illustrating characteristics of the magnetic sensor.

FIG. 11 is a graph illustrating characteristics of the magnetic sensor.

FIG. 11 illustrates characteristics when the width (the width d1) of the portion of the first magnetic element 11E that overlaps the first magnetic member 51 of the configuration of the magnetic sensor 110 is changed. The horizontal axis of FIG. 11 is a ratio WR2 of the width d1 to the third magnetic member width w53 (referring to FIG. 1A). The vertical axis is a magnetic flux density B1 (a relative value) at the position of the first magnetic element 11E when a uniform external magnetic field is applied. In the example of FIG. 11, the widths of the first to fifth magnetic members 51 to 55 are equal to each other. In the example of FIG. 11, the widths of the first to fourth magnetic elements 11E to 14E are equal to each other. FIG. 11 shows the results when the width w1 of the element is 4 μm, 6 μm, or 8 μm.

As shown in FIG. 11, a high magnetic flux density B1 is obtained when the ratio WR2 is not less than 0.1 and not more than 0.4. It is considered that when the ratio WR2 is less than 0.1, for example, the magnetic flux is not easily oriented toward the magnetic elements and flows directly between the multiple magnetic members. It is considered that the leakage of the magnetic flux increases when the ratio WR2 is greater than 0.4.

As shown in FIG. 2A, the portion 21p of the first conductive member 21 overlaps the portion 51p of the first magnetic member 51 in the second direction (the Z-axis direction). As shown in FIG. 2B, the width along the first direction (the X-axis direction) of the portion 21p of the first conductive member 21 is taken as a width dx1. As shown in FIG. 2A, the other portion 21q of the first conductive member 21 overlaps the portion 53p of the third magnetic member 53 in the second direction (the Z-axis direction). The width along the first direction (the X-axis direction) of the other portion 21q of the first conductive member 21 is substantially equal to the width dx1. According to the embodiment, it is favorable for the ratio of the width dx1 to the third magnetic member width w53 (referring to FIG. 1A) to be not more than 0.4.

As shown in FIG. 2A, the portion 22p of the second conductive member 22 overlaps the portion 52p of the second magnetic member 52 in the second direction (the Z-axis direction). As shown in FIG. 2B, the width along the first direction (the X-axis direction) of the portion 22p of the second conductive member 22 is taken as a width dx2. As shown in FIG. 2A, the other portion 22q of the second conductive member 22 overlaps the portion 54p of the fourth magnetic member 54 in the second direction (the Z-axis direction). The width along the first direction (the X-axis direction) of the other portion 22q of the second conductive member 22 is substantially equal to the width dx2. According to the embodiment, it is favorable for the ratio of the width dx2 to the fourth magnetic member width w54 (referring to FIG. 1A) to be not more than 0.4.

As shown in FIG. 2A, the portion 23p of the third conductive member 23 overlaps the other portion 53q of the third magnetic member 53 in the second direction (the Z-axis direction). As shown in FIG. 2B, the width along the first direction (the X-axis direction) of the portion 23p of the third conductive member 23 is taken as a width dx3. As shown in FIG. 2A, the other portion 23q of the third conductive member 23 overlaps the portion 55p of the fifth magnetic member 55 in the second direction (the Z-axis direction). The width along the first direction (the X-axis direction) of the other portion 23q of the third conductive member 23 is substantially equal to the width dx3. According to the embodiment, it is favorable for the width dx3 to be substantially equal to the width dx1. For example, the width dx3 is not less than 0.8 times and not more than 1.2 times the width dx1.

As shown in FIG. 2A, the portion 24p of the fourth conductive member 24 overlaps the other portion 55q of the fifth magnetic member 55 in the second direction (the Z-axis direction). As shown in FIG. 2B, the width along the first direction (the X-axis direction) of the portion 24p of the fourth conductive member 24 is taken as a width dx4. As shown in FIG. 2A, the other portion 24q of the fourth conductive member 24 overlaps the other portion 54q of the fourth magnetic member 54 in the second direction (the Z-axis direction). The width along the first direction (the X-axis direction) of the other portion 24q of the fourth conductive member 24 is substantially equal to the width dx4. According to the embodiment, it is favorable for the width dx4 to be substantially equal to the width dx2. For example, the width dx4 is not less than 0.8 times and not more than 1.2 times the width dx2.

By such a configuration, the magnetic field that is generated by the conductive members is efficiently applied to the magnetic elements via the magnetic members.

Figure 12:
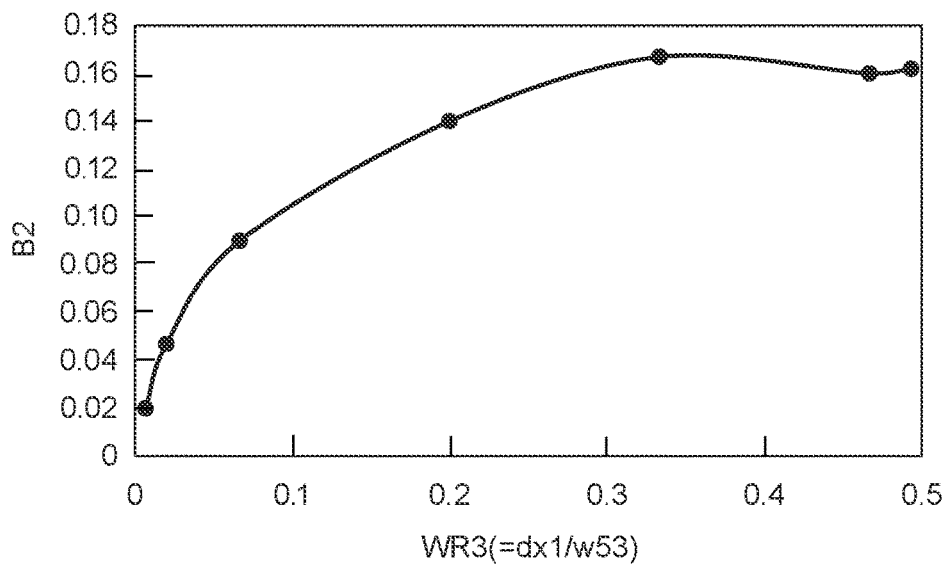
FIG. 12 is a graph illustrating a characteristic of the magnetic sensor.

FIG. 12 is a graph illustrating a characteristic of the magnetic sensor.

FIG. 12 illustrates a characteristic when the width (the relative width) of the portion of the conductive member that overlaps the magnetic member of the configuration of the magnetic sensor 110 is changed. The width dx1 of the portion of the first conductive member 21 that overlaps the first magnetic member 51 is equal to the width of the portion of the first conductive member 21 that overlaps the third magnetic member 53. In the example, the width of the third magnetic member 53 is fixed; and the width of the first conductive member 21 is modified. In the example of FIG. 12, the current density that is supplied to the first conductive member 21 is constant. The current that is supplied is modified according to the modification of the width of the first conductive member 21. The horizontal axis of FIG. 12 is a ratio WR3. The ratio WR3 is the ratio of the width dx1 of the portion of the first conductive member 21 that overlaps the first magnetic member 51 (referring to FIG. 2B) to the third magnetic member width w53 (referring to FIG. 1A). The vertical axis of FIG. 12 is a magnetic flux density B2 (a relative value) at the position of the first magnetic element 11E of the external magnetic field generated by the current supplied to the first conductive member 21.

It can be seen from FIG. 12 that the magnetic flux density B2 increases as the ratio WR3 increases in the range in which the ratio WR3 is 0 to 0.32. In other words, in this range, the magnetic flux density B2 increases as the width of the portion of the conductive member that overlaps the magnetic member increases. When the ratio WR3 is greater than 0.32, the magnetic flux density B2 saturates. When the ratio WR3 is greater than 0.32 and the ratio WR3 is high, much current becomes necessary. Therefore, it is practically favorable for the ratio WR3 to be not more than 0.32. From the perspective of reducing the current consumption, the ratio WR3 may be not more than 0.2. In such a case as well, a high magnetic flux density B2 is obtained compared to when the ratio WR3 is 0. For example, the ratio WR3 may be not less than 0.02. For example, it is favorable for the ratio of the width of the first conductive member 21 that overlaps the third magnetic member 53 to the width w53 along the first direction of the third magnetic member to be not more than 0.32. The ratio may be not less than 0.02.

As shown in FIG. 2B, the distance along the first direction (the X-axis direction) between the first magnetic member 51 and the third magnetic member 53 is taken as a distance g1. The distance along the first direction (the X-axis direction) between the fourth magnetic member 54 and the second magnetic member 52 is taken as a distance g2. The distance along the first direction (the X-axis direction) between the third magnetic member 53 and the fifth magnetic member 55 is taken as a distance g3. The distance along the first direction (the X-axis direction) between the fifth magnetic member 55 and the fourth magnetic member 54 is taken as a distance g4. The distances g1 to g4 are, for example, not less than 1 μm and not more than 5 μm. Thereby, the concentrated magnetic field is efficiently applied to the magnetic elements.

As shown in FIG. 2B, the distance along the second direction (the Z-axis direction) between the magnetic element and the magnetic member is taken as a distance dz. According to the embodiment, it is favorable for the distance dz to be not less than 0.01 μm and not more than 0.5 μm. Thereby, the concentrated magnetic field is efficiently applied to the magnetic element.

Figure 13A:
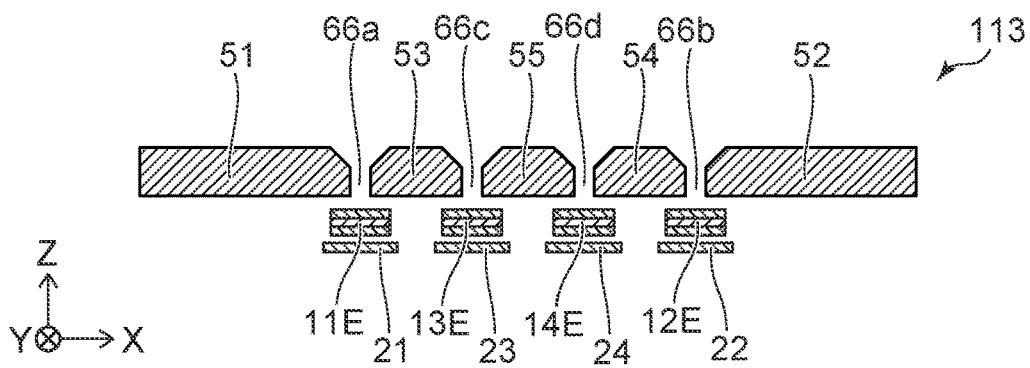
FIGS. 13A and 13B are schematic cross-sectional views illustrating magnetic sensors according to the first embodiment.
Figure 13B:
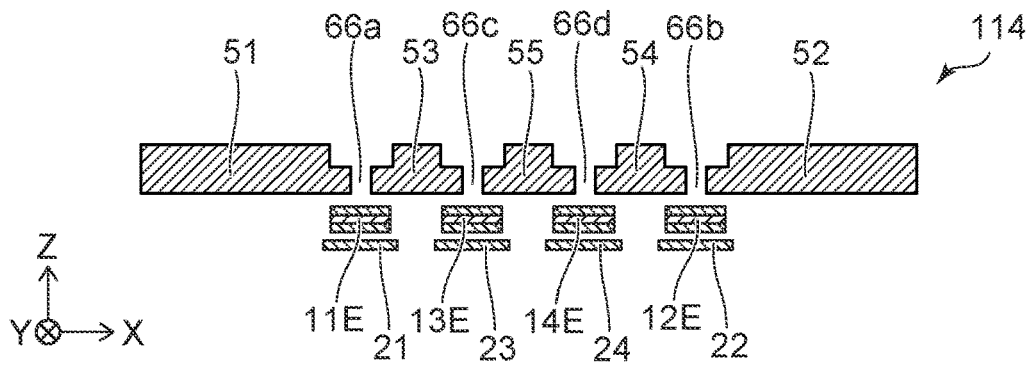

FIGS. 13A and 13B are schematic cross-sectional views illustrating magnetic sensors according to the first embodiment.

As shown in FIGS. 13A and 13B, the thickness of the magnetic member is different by location in a magnetic sensor 113 and a magnetic sensor 114 according to the embodiment. For example, the thickness (the length along the Z-axis direction) at the end portion in the X-axis direction of one magnetic member is less than the thickness at the X-axis direction central portion of the one magnetic member. The magnetic field can be concentrated better at the end portion in the X-axis direction of the magnetic member. The end portion may be tapered as in the magnetic sensor 113. The surface of the end portion may be oblique to the X-axis direction. Otherwise, the configurations of the magnetic sensors 113 and 114 may be similar to those of the magnetic sensors 110 to 112.

Figure 14:
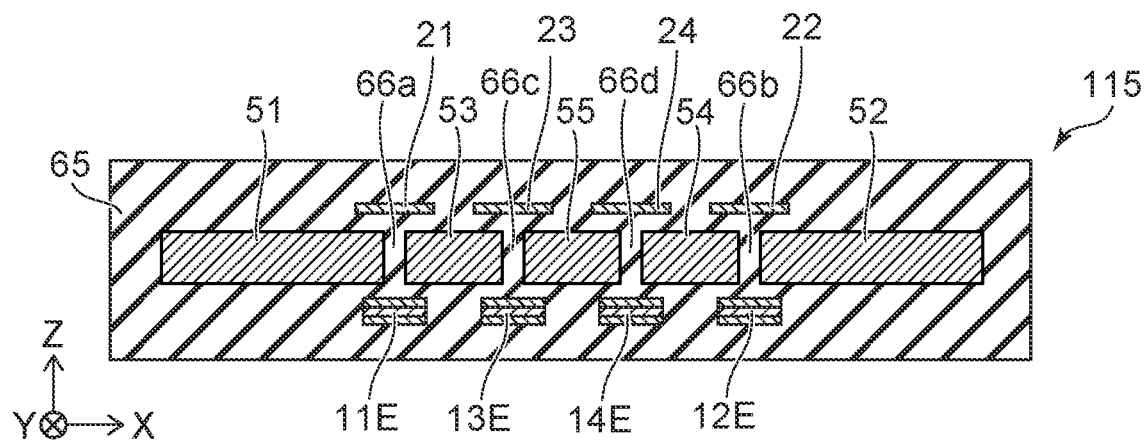
FIG. 14 is a schematic cross-sectional view illustrating a magnetic sensor according to the first embodiment.

FIG. 14 is a schematic cross-sectional view illustrating a magnetic sensor according to the first embodiment.

In the magnetic sensor 115 according to the embodiment as shown in FIG. 14, a portion of the first magnetic member 51 is between the first magnetic element 11E and the first conductive member 21. A portion of the second magnetic member 52 is between the second magnetic element 12E and the second conductive member 22. A portion of the third magnetic member 53 is between the third magnetic element 13E and the third conductive member 23. A portion of the fourth magnetic member 54 is between the fourth magnetic element 14E and the fourth conductive member 24. Otherwise, the configuration of the magnetic sensor 115 may be similar to those of the magnetic sensors 110 to 114. According to the magnetic sensors 113 to 115 as well, a magnetic sensor can be provided in which the sensitivity can be increased.

According to the embodiment, the first to fourth magnetic layers 11 to 14 and the first to fourth counter magnetic layers 110 to 140 include, for example, at least one selected from the group consisting of Fe, Co, and Ni. The first to fifth magnetic members 51 to 55 include, for example, at least one selected from the group consisting of NiFe and CoZrNb. The first to fourth conductive members 21 to 24 include, for example, at least one selected from the group consisting of Cu, Au, and Al.

Second Embodiment

A second embodiment relates to an inspection device. As described below, the inspection device may include a diagnostic device.

Figure 15:
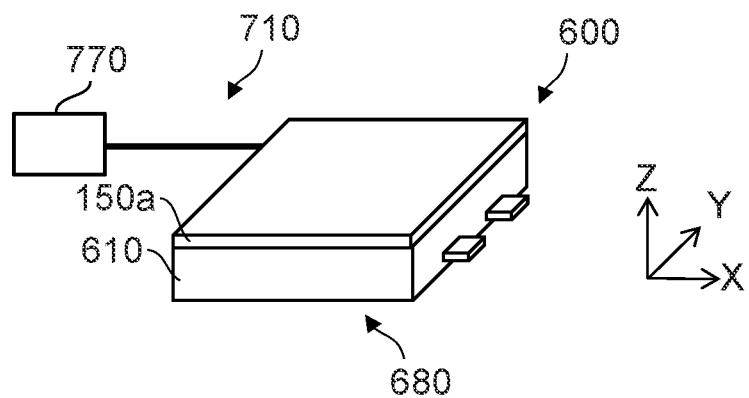
FIG. 15 is a schematic perspective view showing an inspection device according to a second embodiment.

FIG. 15 is a schematic perspective view showing the inspection device according to the second embodiment.

As shown in FIG. 15, the inspection device 710 according to the embodiment includes a magnetic sensor 150a and a processor 770. The magnetic sensor 150a may be the magnetic sensors according to any of the first to fifth embodiments and modifications of the magnetic sensors. The processor 770 processes an output signal obtained from the magnetic sensor 150a. The processor 770 may perform a comparison between a reference value and the signal obtained from the magnetic sensor 150a, etc. The processor 770 is configured to output an inspection result based on the processing result.

For example, an inspection object 680 is inspected by the inspection device 710. The inspection object 680 is, for example, an electronic device (including a semiconductor circuit, etc.). The inspection object 680 may be, for example, a battery 610, etc.

For example, the magnetic sensor 150a according to the embodiment may be used together with the battery 610. For example, a battery system 600 includes the battery 610 and the magnetic sensor 150a. The magnetic sensor 150a can detect a magnetic field generated by a current flowing in the battery 610.

Figure 16:
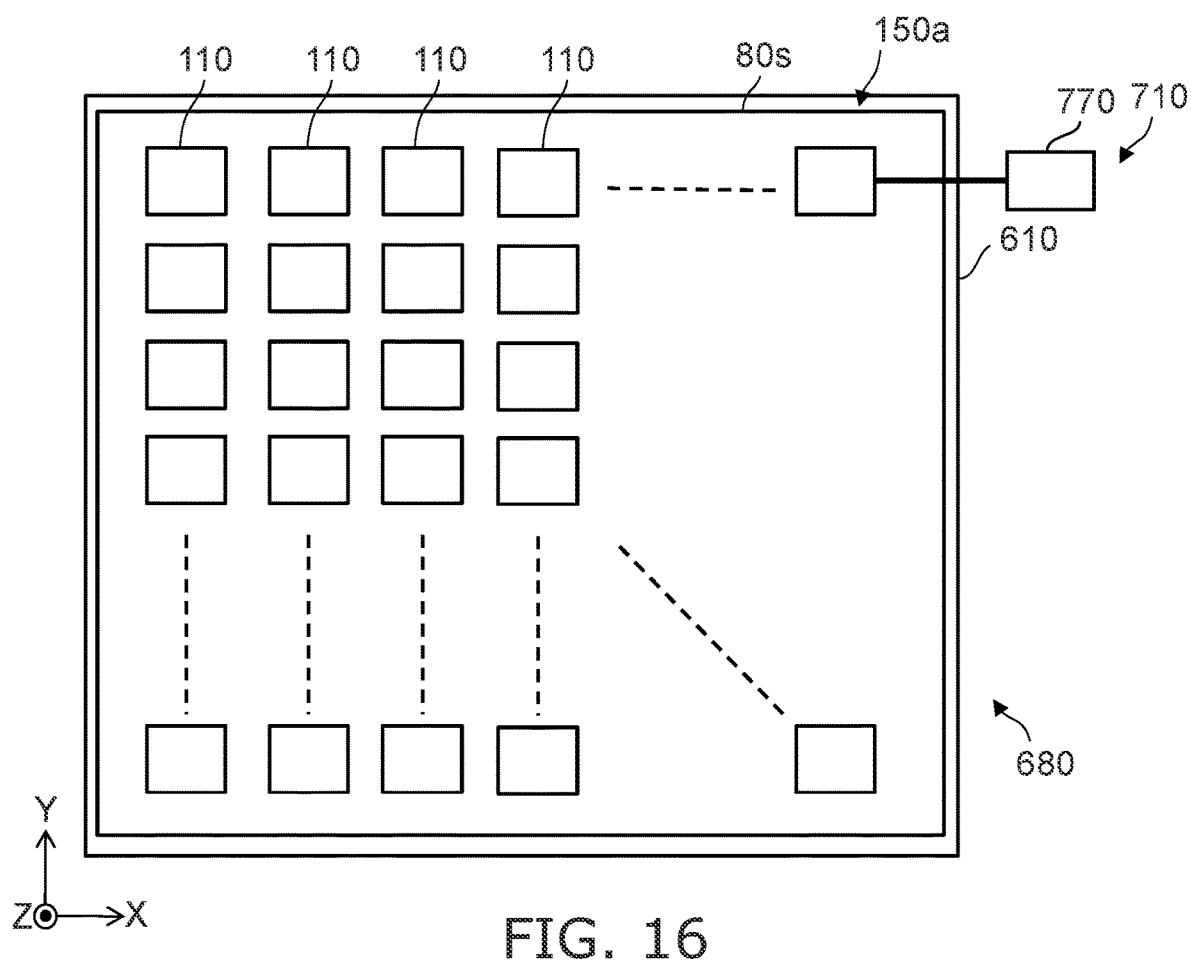
FIG. 16 is a schematic plan view showing the inspection device according to the second embodiment.

FIG. 16 is a schematic plan view showing the inspection device according to the second embodiment.

As shown in FIG. 16, the magnetic sensor 150a includes, for example, multiple magnetic sensors according to the embodiment. In the example, the magnetic sensor 150a includes multiple magnetic sensors (e.g., the magnetic sensor 110, etc.). For example, the multiple magnetic sensors are arranged along two directions (e.g., the X-axis direction and the Y-axis direction). For example, the multiple magnetic sensors 110 are located on a substrate.

The magnetic sensor 150a can detect a magnetic field generated by a current flowing in the inspection object 680 (which may be, for example, the battery 610). For example, an abnormal current flows in the battery 610 when the battery 610 approaches an abnormal state. The change of the state of the battery 610 can be known by the magnetic sensor 150a detecting the abnormal current. For example, the entire battery 610 can be inspected in a short period of time by moving the sensor array in two directions while the magnetic sensor 150a is proximate to the battery 610. The magnetic sensor 150a may be used to inspect the battery 610 in the manufacturing process of the battery 610.

Figure 17:
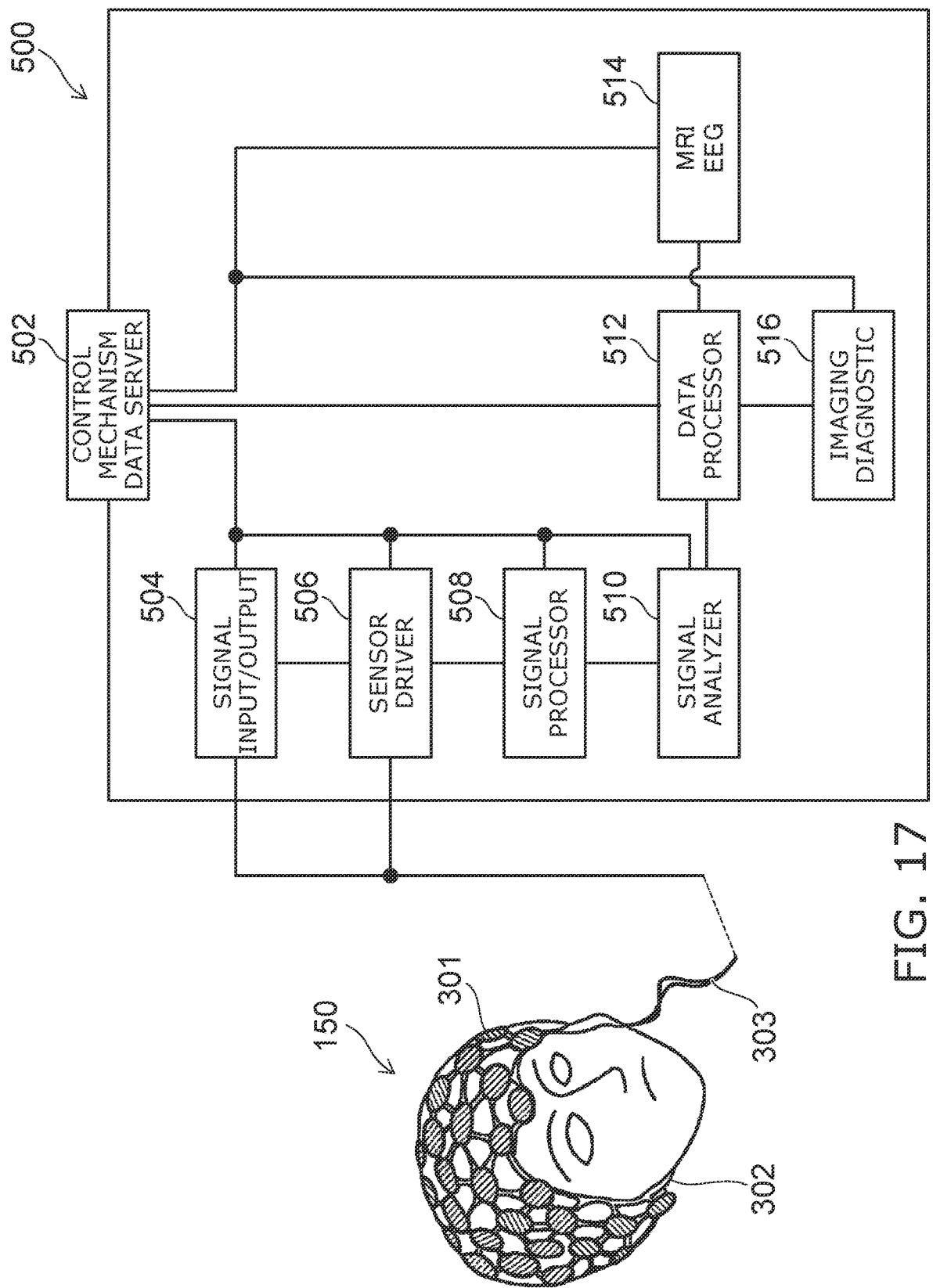
FIG. 17 is a schematic view showing the magnetic sensor and the inspection device according to the second embodiment.

For example, the magnetic sensor according to the embodiment is applicable to the inspection device 710 such as a diagnostic device, etc. FIG. 17 is a schematic view showing the magnetic sensor and the inspection device according to the second embodiment.

As shown in FIG. 17, a diagnostic device 500 is an example of the inspection device 710 and includes a magnetic sensor 150. The magnetic sensor 150 includes the magnetic sensors described in reference to the first to fifth embodiments and modifications of the magnetic sensors.

In the diagnostic device 500, the magnetic sensor 150 is, for example, a magnetoencephalography device. The magnetoencephalography device detects a magnetic field generated by cranial nerves. When the magnetic sensor 150 is used in a magnetoencephalography device, the size of the magnetic element included in the magnetic sensor 150 is, for example, not less than 1 mm but less than 10 mm. The size is, for example, the length including the MFC.

As shown in FIG. 17, the magnetic sensor 150 (the magnetoencephalography device) is mounted to, for example, the head of a human body. The magnetic sensor 150 (the magnetoencephalography device) includes a sensor part 301. The magnetic sensor 150 (the magnetoencephalography device) may include multiple sensor parts 301. The number of the multiple sensor parts 301 is, for example, about 100 (e.g., not less than 50 and not more than 150). The multiple sensor parts 301 are provided on a flexible base body 302.

The magnetic sensor 150 may include, for example, a circuit for differential detection, etc. The magnetic sensor 150 may include a sensor other than a magnetic sensor (e.g., a potential terminal, an acceleration sensor, etc.).

The size of the magnetic sensor 150 is small compared to the size of a conventional SQUID magnetic sensor. Therefore, the mounting of the multiple sensor parts 301 is easy. The mounting of the multiple sensor parts 301 and the other circuits is easy. The multiple sensor parts 301 and the other sensors can be easily mounted together.

The base body 302 may include, for example, an elastic body such as a silicone resin, etc. For example, the multiple sensor parts 301 are linked to each other and provided in the base body 302. For example, the base body 302 can be closely adhered to the head.

An input/output cord 303 of the sensor part 301 is connected with a sensor driver 506 and a signal input/output part 504 of the diagnostic device 500. A magnetic field measurement is performed in the sensor part 301 based on electrical power from the sensor driver 506 and a control signal from the signal input/output part 504. The result is input to the signal input/output part 504. The signal that is obtained by the signal input/output part 504 is supplied to a signal processor 508. Processing such as, for example, the removal of noise, filtering, amplification, signal calculation, etc., are performed in the signal processor 508. The signal that is processed by the signal processor 508 is supplied to a signal analyzer 510. For example, the signal analyzer 510 extracts a designated signal for magnetoencephalography. For example, signal analysis to match the signal phases is performed in the signal analyzer 510.

The output of the signal analyzer 510 (the data for which the signal analysis is finished) is supplied to a data processor 512. Data analysis is performed in the data processor 512. It is possible to include image data such as, for example, MRI (Magnetic Resonance Imaging), etc., in the data analysis. It is possible to include, for example, scalp potential information such as an EEG (Electroencephalogram), etc., in the data analysis. For example, nerve firing point analysis, inverse analysis, or the like is performed by the data analysis.

For example, the result of the data analysis is supplied to an imaging diagnostic part 516. Imaging is performed by the imaging diagnostic part 516. The diagnosis is supported by the imaging.

For example, the series of operations described above is controlled by a control mechanism 502. For example, necessary data such as preliminary signal data, metadata partway through the data processing, or the like is stored in a data server. The data server and the control mechanism may be integrated.

The diagnostic device 500 according to the embodiment includes the magnetic sensor 150, and a processor that processes the output signal obtained from the magnetic sensor 150. The processor includes, for example, at least one of the signal processor 508 or the data processor 512. The processor includes, for example, a computer, etc.

In the magnetic sensor 150 shown in FIG. 17, the sensor part 301 is mounted to the head of a human body. The sensor part 301 may be mounted to the chest of the human body.

Magnetocardiography is possible thereby. For example, the sensor part 301 may be mounted to the abdomen of a pregnant woman. Palmoscopy of the fetus can be performed thereby.

It is favorable for the magnetic sensor device including the participant to be mounted inside a shielded room. For example, the effects of geomagnetism or magnetic noise can be suppressed thereby.

For example, a mechanism may be provided to locally shield the sensor part 301 or the measurement section of the human body. For example, a shield mechanism may be provided in the sensor part 301. For example, the signal analysis or the data processing may be effectively shielded.

According to the embodiment, the base body 302 may be flexible or may be substantially not flexible. In the example shown in FIG. 17, the base body 302 is a continuous membrane that is patterned into a hat-like configuration. The base body 302 may have a net configuration. For example, a good fit is obtained thereby. For example, the adhesion of the base body 302 to the human body is improved. The base body 302 may have a hard helmet-like configuration.

Figure 18:
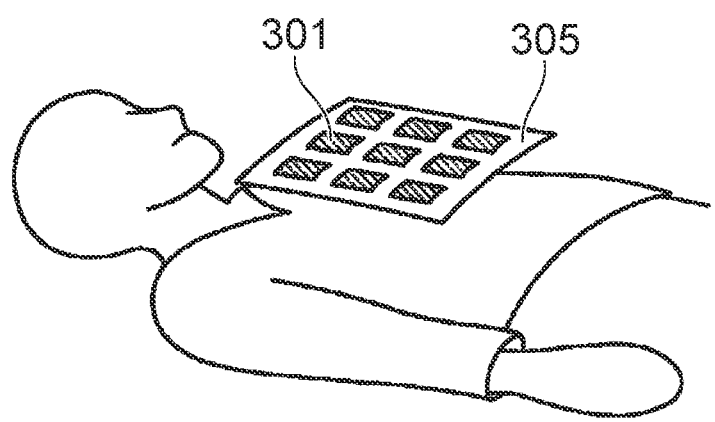
FIG. 18 is a schematic view showing the inspection device according to the embodiment.

FIG. 18 is a schematic view showing the inspection device according to the sixth embodiment.

FIG. 18 is an example of a magnetic detection instrument. In the example shown in FIG. 18, the sensor part 301 is provided on a hard base body 305 having a flat plate shape.

The input and output of the signal obtained from the sensor part 301 in the example shown in FIG. 18 are similar to the input and output described with reference to FIG. 17. The processing of the signal obtained from the sensor part 301 in the example shown in FIG. 18 is similar to the processing described with reference to FIG. 17.

There is a reference example in which a SQUID (Superconducting Quantum Interference Device) magnetic sensor is used as a device to measure a faint magnetic field such as a magnetic field emitted from a living body, etc. Because superconductivity is used in the reference example, the device is large; and the power consumption is large. The load on the measurement object (the patient) is large.

According to the embodiment, the device can be small. The power consumption can be suppressed. The load on the measurement object (the patient) can be reduced. According to the embodiment, the SN ratio of the magnetic field detection can be improved. The sensitivity can be increased.

Embodiments may include the following configurations (e.g., technological proposals).

Configuration 1

A magnetic sensor, comprising:
a first magnetic element;
a second magnetic element;
a third magnetic element located between the first magnetic element and the second magnetic element in a first direction;
a fourth magnetic element located between the third magnetic element and the second magnetic element in the first direction;
a first conductive member;
a second conductive member;
a third conductive member located between the first conductive member and the second conductive member in the first direction;
a fourth conductive member located between the third conductive member and the second conductive member in the first direction;
a first magnetic member;
a second magnetic member;
a third magnetic member located between the first magnetic member and the second magnetic member in the first direction;
a fourth magnetic member located between the third magnetic member and the second magnetic member in the first direction; and
a fifth magnetic member located between the third magnetic member and the fourth magnetic member in the first direction,
the first magnetic element and the first conductive member overlapping a region between the first magnetic member and the third magnetic member in a second direction crossing the first direction,
the second magnetic element and the second conductive member overlapping a region between the fourth magnetic member and the second magnetic member in the second direction,
the third magnetic element and the third conductive member overlapping a region between the third magnetic member and the fifth magnetic member in the second direction,
the fourth magnetic element and the fourth conductive member overlapping a region between the fifth magnetic member and the fourth magnetic member in the second direction.

Configuration 2

The magnetic sensor according to Configuration 1, further comprising:
a first circuit configured to supply a first current to the first to fourth conductive members,
the first current including an alternating current component.

Configuration 3

The magnetic sensor according to Configuration 2, wherein
a direction from one end of the first conductive member toward an other end of the first conductive member is along a third direction crossing a plane including the first and second directions,
a direction from one end of the second conductive member toward an other end of the second conductive member is along the third direction,
a direction from one end of the third conductive member toward an other end of the third conductive member is along the third direction,
a direction from one end of the fourth conductive member toward an other end of the fourth conductive member is along the third direction,
the other end of the first conductive member is electrically connected with the other end of the third conductive member,
the one end of the third conductive member is electrically connected with the one end of the fourth conductive member,
the other end of the fourth conductive member is electrically connected with the other end of the second conductive member, and
the first circuit is configured to supply the first current between the one end of the first conductive member and the one end of the second conductive member.

Configuration 4

The magnetic sensor according to Configuration 3, further comprising:
a second circuit configured to supply a detection current to the first to fourth magnetic elements, a direction from one end of the first magnetic element toward an other end of the first magnetic element being along the third direction, a direction from one end of the second magnetic element toward an other end of the second magnetic element being along the third direction, a direction from one end of the third magnetic element toward an other end of the third magnetic element being along the third direction, a direction from one end of the fourth magnetic element toward an other end of the fourth magnetic element being along the third direction, the other end of the first magnetic element being electrically connected with the other end of the second magnetic element, the one end of the first magnetic element being electrically connected with the one end of the third magnetic element, the other end of the third magnetic element being electrically connected with the other end of the fourth magnetic element, the one end of the fourth magnetic element being electrically connected with the one end of the second magnetic element, the second circuit being configured to supply the detection current between a first connection point and a second connection point, the first connection point being between the other end of the first magnetic element and the other end of the second magnetic element, the second connection point being between the other end of the third magnetic element and the other end of the fourth magnetic element.

Configuration 5

The magnetic sensor according to Configuration 4, further comprising:

a third circuit, the third circuit being configured to detect a change of a potential between a third connection point and a fourth connection point, the third connection point being between the one end of the first magnetic element and the one end of the third magnetic element, the fourth connection point being between the one end of the fourth magnetic element and the one end of the second magnetic element.

Configuration 6

The magnetic sensor according to any one of Configurations 1 to 5, wherein a portion of the first magnetic element and a portion of the first conductive member overlap at least a portion of the first magnetic member in the second direction, an other portion of the first magnetic element and an other portion of the first conductive member overlap a portion of the third magnetic member in the second direction, a portion of the second magnetic element and a portion of the second conductive member overlap at least a portion of the second magnetic member in the second direction, an other portion of the second magnetic element and an other portion of the second conductive member overlap a portion of the fourth magnetic member in the second direction, a portion of the third magnetic element and a portion of the third conductive member overlap an other portion of the third magnetic member in the second direction, an other portion of the third magnetic element and an other portion of the third conductive member overlap a portion of the fifth magnetic member in the second direction, a portion of the fourth magnetic element and a portion of the fourth conductive member overlap an other portion of the fifth magnetic member in the second direction, and an other portion of the fourth magnetic element and an other portion of the fourth conductive member overlap an other portion of the fourth magnetic member in the second direction.

Configuration 7

The magnetic sensor according to any one of Configurations 1 to 6, wherein the first magnetic element has a first width along the first direction, a portion of the first magnetic element overlaps the at least a portion of the first magnetic member in the second direction, and a ratio of a width along the first direction of the portion of the first magnetic element to the first width is not less than 0.1 and not more than 0.4.

Configuration 8

The magnetic sensor according to any one of Configurations 1 to 7, wherein a first magnetic member thickness along the second direction of the first magnetic member is greater than a fifth magnetic member thickness along the second direction of the fifth magnetic member.

Configuration 9

The magnetic sensor according to Configuration 8, wherein a third magnetic member thickness along the second direction of the third magnetic member is less than the first magnetic member thickness.

Configuration 10

The magnetic sensor according to any one of Configurations 1 to 7, wherein a first magnetic member width along the first direction of the first magnetic member is greater than a fifth magnetic member width along the first direction of the fifth magnetic member.

Configuration 11

The magnetic sensor according to Configuration 10, wherein a third magnetic member width along the first direction of the third magnetic member is less than the first magnetic member width.

Configuration 12

The magnetic sensor according to any one of Configurations 3 to 5, wherein a first magnetic member length along the third direction of the first magnetic member is greater than a fifth magnetic member length along the third direction of the fifth magnetic member.

Configuration 13

The magnetic sensor according to Configuration 12, wherein a third magnetic member length along the third direction of the third magnetic member is less than the first magnetic member length.

Configuration 14

The magnetic sensor according to any one of Configurations 3 to 5, wherein the first magnetic member includes a first magnetic member end and a first magnetic member other-end, the first magnetic member other-end is between the first magnetic member end and the third magnetic member in the first direction, and a length along the third direction of the first magnetic member increases in an orientation from the first magnetic member other-end toward the first magnetic member end.

Configuration 15

The magnetic sensor according to any one of Configurations 1 to 14, wherein an electrical resistance of the first magnetic element has a first value when a first magnetic field is applied to the first magnetic element, the electrical resistance has a second value when a second magnetic field is applied to the first magnetic element, the electrical resistance has a third value when a third magnetic field is applied to the first magnetic element, an absolute value of the first magnetic field is less than an absolute value of the second magnetic field and less than an absolute value of the third magnetic field, an orientation of the second magnetic field is opposite to an orientation of the third magnetic field, and the first value is less than the second and third values, or the first value is greater than the second and third values.

Configuration 16

The magnetic sensor according to any one of Configurations 1 to 14, wherein the electrical resistance of the first magnetic element has a first value when a first-value current is supplied to the first conductive member, the electrical resistance has a second value when a second-value current is supplied to the first conductive member, the electrical resistance has a third value when a third-value current is supplied to the first conductive member, an absolute value of the first-value current is less than an absolute value of the second-value current and less than an absolute value of the third-value current, an orientation of the second-value current is opposite to an orientation of the third-value current, and the first value is less than the second and third values, or the first value is greater than the second and third values.

Configuration 17

The magnetic sensor according to any one of Configurations 1 to 14, wherein an electrical resistance of the first magnetic element has an even-function change with respect to a magnetic field applied to the first magnetic element.

Configuration 18

The magnetic sensor according to any one of Configurations 1 to 17, wherein at least a portion of the first magnetic element is between the first conductive member and the first magnetic member.

Configuration 19

The magnetic sensor according to any one of Configurations 1 to 18, wherein the first magnetic element includes:
a first magnetic layer;
a first counter magnetic layer; and
a first nonmagnetic layer located between the first magnetic layer and the first counter magnetic layer, a direction from the first magnetic layer toward the first counter magnetic layer is along the second direction, the second magnetic element includes:
a second magnetic layer;
a second counter magnetic layer; and
a second nonmagnetic layer located between the second magnetic layer and the second counter magnetic layer, a direction from the second magnetic layer toward the second counter magnetic layer is along the second direction, the third magnetic element includes:
a third magnetic layer;
a third counter magnetic layer; and
a third nonmagnetic layer located between the third magnetic layer and the third counter magnetic layer, a direction from the third magnetic layer toward the third counter magnetic layer is along the second direction, the fourth magnetic element includes:
a fourth magnetic layer;
a fourth counter magnetic layer; and
a fourth nonmagnetic layer located between the fourth magnetic layer and the fourth counter magnetic layer, and a direction from the fourth magnetic layer toward the fourth counter magnetic layer is along the second direction.

Configuration 20

The magnetic sensor according to any one of Configurations 1 to 19, wherein a ratio of a width of the first conductive member overlapping the third magnetic member to a width along the first direction of the third magnetic member is not more than 0.32.

Configuration 21

An inspection device, comprising:
the magnetic sensor according to any one of Configurations 1 to 20; and
a processor configured to process a signal output from the magnetic sensor.

According to embodiments, a magnetic sensor and an inspection device can be provided in which the sensitivity can be increased.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in magnetic sensors such as magnetic elements, magnetic layers, nonmagnetic layers, magnetic members, conductive members, circuits, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all magnetic sensors, and inspection devices practicable by an appropriate design modification by one skilled in the art based on the magnetic sensors, and the inspection devices described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A magnetic sensor, comprising:
a first magnetic element;
a second magnetic element;
a third magnetic element located between the first magnetic element and the second magnetic element in a first direction;
a fourth magnetic element located between the third magnetic element and the second magnetic element in the first direction;
a first conductive member;
a second conductive member;
a third conductive member located between the first conductive member and the second conductive member in the first direction;
a fourth conductive member located between the third conductive member and the second conductive member in the first direction;
a first magnetic member;
a second magnetic member;
a third magnetic member located between the first magnetic member and the second magnetic member in the first direction;
a fourth magnetic member located between the third magnetic member and the second magnetic member in the first direction; and
a fifth magnetic member located between the third magnetic member and the fourth magnetic member in the first direction,
the first magnetic element and the first conductive member overlapping a region between the first magnetic member and the third magnetic member in a second direction crossing the first direction,
the second magnetic element and the second conductive member overlapping a region between the fourth magnetic member and the second magnetic member in the second direction,
the third magnetic element and the third conductive member overlapping a region between the third magnetic member and the fifth magnetic member in the second direction,
the fourth magnetic element and the fourth conductive member overlapping a region between the fifth magnetic member and the fourth magnetic member in the second direction.

2. The sensor according to claim 1, further comprising:
a first circuit configured to supply a first current to the first to fourth conductive members,
the first current including an alternating current component.

3. The sensor according to claim 2, wherein
a direction from one end of the first conductive member toward an other end of the first conductive member is along a third direction crossing a plane including the first and second directions,
a direction from one end of the second conductive member toward an other end of the second conductive member is along the third direction,
a direction from one end of the third conductive member toward an other end of the third conductive member is along the third direction,
a direction from one end of the fourth conductive member toward an other end of the fourth conductive member is along the third direction,
the other end of the first conductive member is electrically connected with the other end of the third conductive member,
the one end of the third conductive member is electrically connected with the one end of the fourth conductive member,
the other end of the fourth conductive member is electrically connected with the other end of the second conductive member, and
the first circuit is configured to supply the first current between the one end of the first conductive member and the one end of the second conductive member.

4. The sensor according to claim 3, further comprising:
a second circuit configured to supply a detection current to the first to fourth magnetic elements,
a direction from one end of the first magnetic element toward an other end of the first magnetic element being along the third direction,
a direction from one end of the second magnetic element toward an other end of the second magnetic element being along the third direction,
a direction from one end of the third magnetic element toward an other end of the third magnetic element being along the third direction,
a direction from one end of the fourth magnetic element toward an other end of the fourth magnetic element being along the third direction,
the other end of the first magnetic element being electrically connected with the other end of the second magnetic element,
the one end of the first magnetic element being electrically connected with the one end of the third magnetic element,
the other end of the third magnetic element being electrically connected with the other end of the fourth magnetic element,
the one end of the fourth magnetic element being electrically connected with the one end of the second magnetic element,
the second circuit being configured to supply the detection current between a first connection point and a second connection point,
the first connection point being between the other end of the first magnetic element and the other end of the second magnetic element,
the second connection point being between the other end of the third magnetic element and the other end of the fourth magnetic element.

5. The sensor according to claim 4, further comprising:
a third circuit,
the third circuit being configured to detect a change of a potential between a third connection point and a fourth connection point,
the third connection point being between the one end of the first magnetic element and the one end of the third magnetic element,
the fourth connection point being between the one end of the fourth magnetic element and the one end of the second magnetic element.

6. The sensor according to claim 1, wherein
a portion of the first magnetic element and a portion of the first conductive member overlap at least a portion of the first magnetic member in the second direction,
an other portion of the first magnetic element and an other portion of the first conductive member overlap a portion of the third magnetic member in the second direction,
a portion of the second magnetic element and a portion of the second conductive member overlap at least a portion of the second magnetic member in the second direction,
an other portion of the second magnetic element and an other portion of the second conductive member overlap a portion of the fourth magnetic member in the second direction,
a portion of the third magnetic element and a portion of the third conductive member overlap an other portion of the third magnetic member in the second direction,
an other portion of the third magnetic element and an other portion of the third conductive member overlap a portion of the fifth magnetic member in the second direction,
a portion of the fourth magnetic element and a portion of the fourth conductive member overlap an other portion of the fifth magnetic member in the second direction, and
an other portion of the fourth magnetic element and an other portion of the fourth conductive member overlap an other portion of the fourth magnetic member in the second direction.

7. The sensor according to claim 1, wherein
the first magnetic element has a first width along the first direction,
a portion of the first magnetic element overlaps the at least a portion of the first magnetic member in the second direction, and
a ratio of a width along the first direction of the portion of the first magnetic element to the first width is not less than 0.1 and not more than 0.4.

8. The sensor according to claim 1, wherein
a first magnetic member thickness along the second direction of the first magnetic member is greater than a fifth magnetic member thickness along the second direction of the fifth magnetic member.

9. The sensor according to claim 8, wherein
a third magnetic member thickness along the second direction of the third magnetic member is less than the first magnetic member thickness.

10. The sensor according to claim 1, wherein
a first magnetic member width along the first direction of the first magnetic member is greater than a fifth magnetic member width along the first direction of the fifth magnetic member.

11. The sensor according to claim 10, wherein
a third magnetic member width along the first direction of the third magnetic member is less than the first magnetic member width.

12. The sensor according to claim 3, wherein
a first magnetic member length along the third direction of the first magnetic member is greater than a fifth magnetic member length along the third direction of the fifth magnetic member.

13. The sensor according to claim 12, wherein
a third magnetic member length along the third direction of the third magnetic member is less than the first magnetic member length.

14. The sensor according to claim 3, wherein
the first magnetic member includes a first magnetic member end and a first magnetic member other-end,
the first magnetic member other-end is between the first magnetic member end and the third magnetic member in the first direction, and
a length along the third direction of the first magnetic member increases in an orientation from the first magnetic member other-end toward the first magnetic member end.

15. The sensor according to claim 1, wherein
an electrical resistance of the first magnetic element has a first value when a first magnetic field is applied to the first magnetic element,
the electrical resistance has a second value when a second magnetic field is applied to the first magnetic element,
the electrical resistance has a third value when a third magnetic field is applied to the first magnetic element,
an absolute value of the first magnetic field is less than an absolute value of the second magnetic field and less than an absolute value of the third magnetic field,
an orientation of the second magnetic field is opposite to an orientation of the third magnetic field, and
the first value is less than the second and third values, or the first value is greater than the second and third values.

16. The sensor according to claim 1, wherein
the electrical resistance of the first magnetic element has a first value when a first-value current is supplied to the first conductive member,
the electrical resistance has a second value when a second-value current is supplied to the first conductive member,
the electrical resistance has a third value when a third-value current is supplied to the first conductive member,
an absolute value of the first-value current is less than an absolute value of the second-value current and less than an absolute value of the third-value current,
an orientation of the second-value current is opposite to an orientation of the third-value current, and
the first value is less than the second and third values, or the first value is greater than the second and third values.

17. The sensor according to claim 1, wherein
an electrical resistance of the first magnetic element has an even-function change with respect to a magnetic field applied to the first magnetic element.

18. The sensor according to claim 1, wherein
at least a portion of the first magnetic element is between the first conductive member and the first magnetic member.

19. The sensor according to claim 1, wherein
the first magnetic element includes:
  a first magnetic layer;
  a first counter magnetic layer; and
  a first nonmagnetic layer located between the first magnetic layer and the first counter magnetic layer,
a direction from the first magnetic layer toward the first counter magnetic layer is along the second direction,
the second magnetic element includes:
  a second magnetic layer;
  a second counter magnetic layer; and
  a second nonmagnetic layer located between the second magnetic layer and the second counter magnetic layer, a direction from the second magnetic layer toward the second counter magnetic layer is along the second direction, the third magnetic element includes:
- a third magnetic layer;
- a third counter magnetic layer; and
- a third nonmagnetic layer located between the third magnetic layer and the third counter magnetic layer, a direction from the third magnetic layer toward the third counter magnetic layer is along the second direction, the fourth magnetic element includes:
- a fourth magnetic layer;
- a fourth counter magnetic layer; and
- a fourth nonmagnetic layer located between the fourth magnetic layer and the fourth counter magnetic layer, and a direction from the fourth magnetic layer toward the fourth counter magnetic layer is along the second direction.

20. An inspection device, comprising:

the magnetic sensor according to claim 1; and a processor configured to process a signal output from the magnetic sensor.

\* \* \* \* \*